US006564087B1

(12) United States Patent
Pitris et al.

(10) Patent No.: US 6,564,087 B1
(45) Date of Patent: May 13, 2003

(54) FIBER OPTIC NEEDLE PROBES FOR OPTICAL COHERENCE TOMOGRAPHY IMAGING

(75) Inventors: Constantinos Pitris, Boston, MA (US); Stephen A. Boppart, Boston, MA (US); Xingde Li, Beverly, MA (US); Mark Brezinski, Malden, MA (US); Eric Swanson, Acton, MA (US); Edward McNamara, Chelmsford, MA (US); James G. Fujimoto, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/359,574

(22) Filed: Jul. 22, 1999

Related U.S. Application Data

(63) Continuation-in-part of application No. 08/916,759, filed on Aug. 19, 1997, now Pat. No. 5,784,352, which is a continuation-in-part of application No. 08/607,787, filed on Feb. 27, 1996, now Pat. No. 6,134,003, which is a continuation-in-part of application No. 08/577,366, filed on Dec. 22, 1995, now Pat. No. 5,748,598, which is a continuation of application No. 08/492,738, filed on Jun. 21, 1995, now abandoned, and a continuation-in-part of application No. 08/252,940, filed on Jun. 2, 1994, now abandoned, which is a continuation-in-part of application No. 08/033,194, filed on Mar. 16, 1993, now Pat. No. 5,459,570, which is a continuation of application No. 07/692,877, filed on Apr. 29, 1991, now abandoned.

(60) Provisional application No. 60/116,859, filed on Jan. 22, 1999.

(51) Int. Cl.[7] ............................................. A61B 5/00
(52) U.S. Cl. ............................................. 600/478
(58) Field of Search ................. 600/473, 476, 600/478, 114, 104; 604/22, 164.01, 164.02; 385/12

(56) References Cited

U.S. PATENT DOCUMENTS 3,556,079 A    1/1971  Omizo .......................... 128/2

(List continued on next page.)

FOREIGN PATENT DOCUMENTS

EP    0 501 034 A1    9/1992

(List continued on next page.)

OTHER PUBLICATIONS

Huang, et al., "Optical coherence tomography." Science 254: 1178–1181 (Nov. 1991).

(List continued on next page.)

Primary Examiner—Marvin M. Lateef
Assistant Examiner—Eleni Mantis Mercader
(74) Attorney, Agent, or Firm—Testa, Hurwitz & Thibeault, LLP

(57) ABSTRACT

A fiber optic needle probe for measuring or imaging the internal structure of a specimen includes a needle defining a bore, an optical fiber substantially positioned within the bore, and a beam director in optical communication with the optical fiber. At least a portion of the wall of the needle is capable of transmitting light. The beam director directs light from the optical fiber to an internal structure being imaged and receives light from the structure through a transparent portion of the wall. An actuating device causes motion of any, or all of, the needle, optical fiber, and beam director to scan the internal structure of the specimen. The fiber optic needle probe allows imaging inside a solid tissue or organ without intraluminal insertion. When used in conjunction with an OCT imaging system, the fiber optic needle probe enables tomographic imaging of the microstructure of internal organs and tissues which were previously impossible to image in a living subject.

22 Claims, 13 Drawing Sheets

U.S. PATENT DOCUMENTS

| | | | |
|---|---|---|---|
| 3,941,121 A * | 3/1976 | Olinger et al. | 128/6 |
| 3,961,621 A | 6/1976 | Northeved | 128/2 B |
| 4,058,114 A | 11/1977 | Soldner | 128/2 V |
| 4,336,809 A | 6/1982 | Clark | 128/665 |
| 4,834,102 A | 5/1989 | Schwarzchild et al. | 128/662.06 |
| 4,887,606 A | 12/1989 | Yock et al. | 128/662.05 |
| 5,034,613 A | 7/1991 | Denk et al. | 250/458.1 |
| 5,112,299 A * | 5/1992 | Pascaloff | 604/22 |
| 5,127,405 A * | 7/1992 | Alcala et al. | 600/342 |
| 5,257,991 A | 11/1993 | Fletcher et al. | 606/17 |
| 5,280,788 A * | 1/1994 | Janes et al. | 600/476 |
| 5,303,026 A | 4/1994 | Strobl et al. | 356/318 |
| 5,305,759 A | 4/1994 | Kaneko et al. | 128/665 |
| 5,321,501 A | 6/1994 | Swanson et al. | 356/345 |
| 5,343,543 A | 8/1994 | Novak, Jr. et al. | 385/31 |
| 5,354,294 A | 10/1994 | Chou | 606/16 |
| 5,366,456 A | 11/1994 | Rink et al. | 606/16 |
| 5,370,649 A | 12/1994 | Gardetto et al. | 606/17 |
| 5,383,467 A | 1/1995 | Auer et al. | 128/664 |
| 5,401,270 A | 3/1995 | Müller et al. | 606/13 |
| 5,421,337 A | 6/1995 | Richards-Kortum et al. | 128/665 |
| 5,421,339 A | 6/1995 | Ramanujam et al. | 128/665 |
| 5,428,699 A | 6/1995 | Pon | 385/31 |
| 5,439,000 A | 8/1995 | Gunderson et al. | 128/664 |
| 5,459,570 A | 10/1995 | Swanson et al. | 356/345 |
| 5,483,958 A * | 1/1996 | Merberg et al. | 250/368 |
| 5,490,521 A | 2/1996 | Davis et al. | 128/662.02 |
| 5,495,541 A | 2/1996 | Murray et al. | 385/33 |
| 5,509,917 A | 4/1996 | Cecchetti et al. | 606/15 |
| 5,537,499 A | 7/1996 | Brekke | 385/31 |
| 5,562,100 A | 10/1996 | Kittrell et al. | 128/665 |
| 5,562,657 A | 10/1996 | Griffin | 606/17 |
| 5,571,099 A | 11/1996 | Purcell, Jr. et al. | 606/17 |
| 5,601,087 A | 2/1997 | Gunderson et al. | 128/664 |
| 5,612,540 A | 3/1997 | Richards-Kortum et al. | 250/461.2 |
| 5,623,932 A | 4/1997 | Ramanujam et al. | 128/665 |
| 5,697,373 A | 12/1997 | Richards-Kortum et al. | 128/664 |
| 5,699,795 A | 12/1997 | Richards-Kortum et al. | 128/634 |
| 5,715,825 A | 2/1998 | Crowley | 128/602.06 |
| 5,752,518 A | 5/1998 | McGee et al. | 128/662.06 |
| 5,762,613 A | 6/1998 | Sutton et al. | 600/564 |
| 5,772,657 A | 6/1998 | Hmelar et al. | 606/15 |
| 5,954,655 A * | 9/1999 | Hussman | 128/898 |
| 6,007,481 A * | 12/1999 | Rick et al. | 600/411 |
| 2001/0047135 A1 * | 11/2001 | Daniels et al. | 600/466 |

FOREIGN PATENT DOCUMENTS

| | | |
|---|---|---|
| GB | 8611055 | 12/1987 |
| JP | 6-35946 | 6/1994 |
| WO | 92/14399 | 9/1992 |
| WO | 95/28129 | 10/1995 |
| WO | WO 97/32182 | 9/1997 |
| WO | 97/41767 | 11/1997 |
| WO | 98/27865 | 7/1998 |
| WO | 98/38907 | 11/1998 |

OTHER PUBLICATIONS

Tearney, et al., "Scanning single mode catheter/endoscope for optical coherence tomography." Opt. Lett. 21: 543–545 (Apr. 1996).

Tearney, et al., "In vivo endoscopic optical biopsy with optical coherence tomography." Science 276: 2037–2039 (Jun. 1997).

Fujimoto, et al., "Optical biopsy and imaging using optical coherence tomography." Nature Medicine 1(9): 970–972 (Sep. 1995).

Brezinski, et al., "Optical Biopsy with optical coherence tomography: feasibility for surgical diagnostics." Journal of Surgical Research 71(1): 32–40 (Jul. 15, 1997).

Tearney, et al., "Optical biopsy in human urologic tissue using optical coherence tomography." The Journal of Urology 157(5): 1915–1919 (May 1997).

Boppart, et al., "High–resolution optical coherence tomography–guided laser ablation of surgical tissue." Journal of Surgical Research 82(2): 275–284 (Apr. 1999).

Boppart, et al., "Optical coherence tomography for neurosurgical imaging of human intracortical melanoma." Neurosurgery 43(4): 834–841 (Oct. 1998).

Herrmann, et al., "Two– and three–dimensional high–resolution imaging of the human oviduct with optical coherence tomography." Fertility and Sterility 70(1): 155–158 (Jul. 1998).

Brezinski, et al., "Assessing atherosclerotic plaque morphology: comparison of optical coherence tomography and high frequency intravascular ultrasound." Heart 77(5): 397–403 (May 1997).

Tearney, et al., "Optical biopsy in human pancreatobiliary tissue using optical coherence tomography." Digestive Diseases and Sciences 43(6): 1193–1199 (Jun. 1998).

Pitris, et al., "High resolution imaging of the upper respiratory tract with optical coherence tomography." Respiratory and Critical Care Medicine 157(5): 1640–1644 (May 1998).

Brezinski, et al., "Optical biopsy with optical coherence tomography" Advances in Optical Biopsy and Optical Mammography 838: 68–74 (1998).

Fujimoto, et al., "New technology for high–speed and high–resolution optical coherence tomography" Advances in Optical Biopsy and Optical Mammography 838: 95–107 (1998).

Tearney, et al., "Optical biopsy in human gastrointestinal tissue using optical coherence tomography." The American Journal of Gastroenterology 92(10): 1800–1804 (Oct. 1997).

Fujimoto, et al., "High resolution in vivo intra–arterial imaging with optical coherence tomography." Heart 82(2): 128–133 (Aug. 1999).

Boppart, et al., "Imaging developing neural morphology using optical coherence tomography" Journal of Neuroscience Methods 70(1): 65–72 (Dec. 1996).

Roper, et al., "In vivo detection of experimentally induced cortical dysgenesis in the adult rat neocortex using optical coherence tomography" Journal of Neuroscience Methods 80(1): 91–98 (Mar. 13, 1998).

Boppart, et al., "Intraoperative assessment of microsurgery with three–dimensional optical coherence tomography" Radiology 208(1): 81–86 (Jul. 1998).

Tearney, et al., "In vivo endoscopic optical biopsy with optical coherence tomography" Science 276: 2037–2039 (Jun. 27, 1997).

Herrmann, et al., "High resolution imaging of normal and osteoarthritic cartilage with optical coherence tomography" The Journal of Rheumatology 26(3): 627–635 (Mar. 1999).

Boppart, et al., "In vivo cellular optical coherence tomography imaging." Nature Medicine 4(7): 861–865 (Jul. 1998).

Pitris, et al., "High resolution imaging of gynecologic neoplasms using optical coherence tomography." Obstetrics & Gynecology 93(1): 135–139 (Jan. 1999).

* cited by examiner

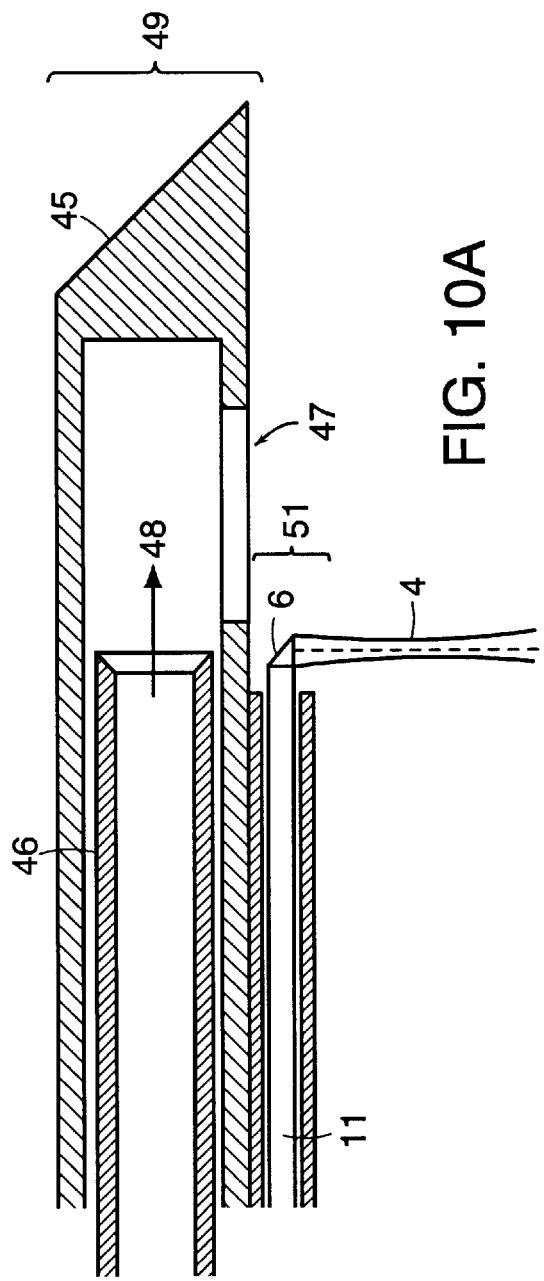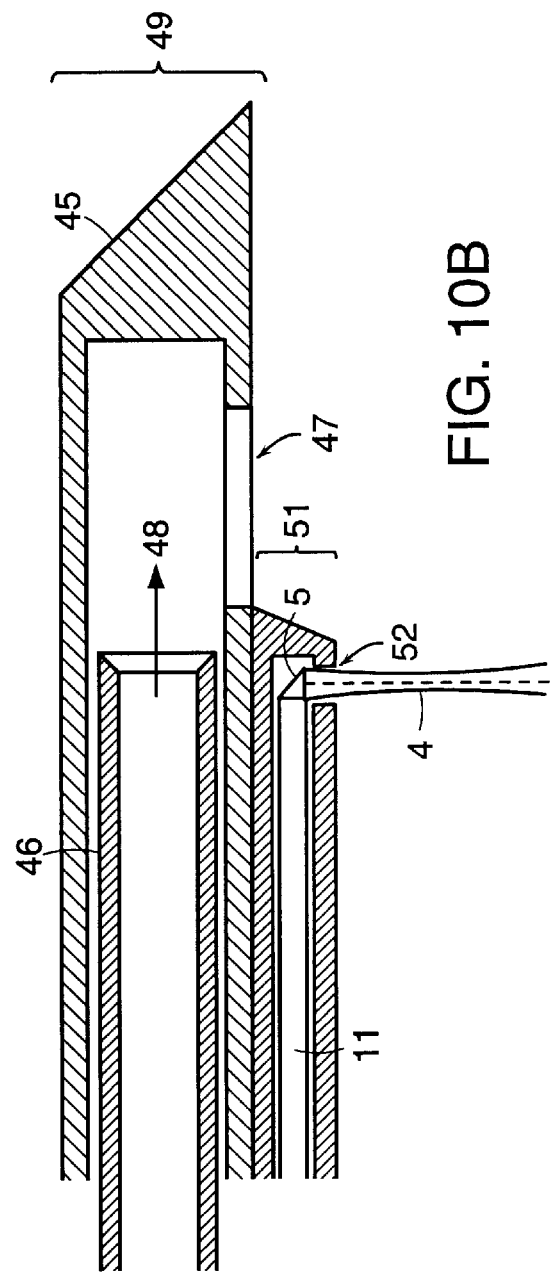

FIBER OPTIC NEEDLE PROBES FOR OPTICAL COHERENCE TOMOGRAPHY IMAGING

CROSS-REFERENCE TO RELATED APPLICATIONS

This Application claims priority under 35 U.S.C. §119(e) to U.S. Provisional Application Serial No. 60/116,859, filed Jan. 22, 1999, the entirety of which is incorporated by reference herein. This application also claims priority under 35 U.S.C. §120 as a continuation-in-part application to U.S. patent application Ser. No. 08/607,787, filed Feb. 27, 1996, and now U.S. Pat. No. 6,134,003 which is a continuation-in-part application of U.S. patent application Ser. No. 08/577,366, filed Dec. 22, 1995, now U.S. Pat. No. 5,748,598, and is also a continuation-in-part application of U.S. patent application Ser. No. 08/916,759, filed Aug. 19, 1997, now issued as U.S. Pat. No. 5,784,352, which is an FWC application of U.S. patent application Ser. No. 08/492,738, filed Jun. 21, 1995, now abandoned, and is also a continuation-in-part application of U.S. patent application Ser. No. 08/252,940, filed Jun. 2, 1994, now abandoned, which is a continuation-in-part of U.S. patent application Ser. No. 08/033,194, filed Mar. 16, 1993, now U.S. Pat. No. 5,459,570, which is a continuation of U.S. patent application Ser. No. 07/692,877, filed Apr. 29, 1991, now abandoned. The entirety of these applications are hereby incorporated herein by reference.

GOVERNMENT SUPPORT

This invention was made with government support under Contract Numbers NIH-1-RO1 EY11289, NIH-1-RO1-CA75289, and NIH-1-R29-HL55686-01A1 from the National Institutes of Health, Contract N00014-94-1-0717 from the Office of Naval Research, and Contract 96-0205 awarded by the Whitaker Foundation.

FIELD OF THE INVENTION

The present invention relates generally to fiber optic needle probes adapted for use in optical imaging systems.

BACKGROUND OF THE INVENTION

Optical imaging systems such as optical coherence tomography (OCT) systems generate images or measurements by measuring the intensity of light backscattered or backreflected from a specimen and providing a gray scale or false color two-dimensional representation of this light intensity in a plane or cross-section through the object being imaged or measured. OCT enables the nonexcisional, in situ, real-time imaging of microstructure in a specimen with a resolution of approximately 2 to 10 microns.

An OCT system can be separated into an imaging engine and probes. The imaging engine contains the optical light source, optical interferometer and other optical detection elements, as well as electronics, motors, controller(s), and computers for image generation and display. The probes are modules which are attached to the engine and direct light to and from the specimen which is to be measured or imaged.

In spite of advances in probe construction and in related delivery and scanning techniques, all previous OCT systems have had the major limitation of being applicable only for imaging internal structures which are accessible from existing orifices of the body or intraluminally from inside a hollow organ. There remains a critical, unfilled need for a new apparatus which enables optical coherence tomographic imaging inside solid tissues or organs without the need for intraluminal insertion.

SUMMARY OF THE INVENTION

The present invention provides a fiber optic needle probe adapted for use in an optical imaging system, particularly for use in imaging solid tissues and organs. In biological and medical applications, the fiber optic needle probe can be inserted directly into a solid tissue or organ or through a tissue wall into the lumen of a hollow organ or space (such as into a sinus cavity or into a blood vessel). The fiber optic needle probe can be inserted with minimal trauma into a tissue because of its small diameter. Thus, the fiber optic needle probe of the present invention enables optical measurement and imaging in regions of the body which are not accessible using existing catheter, endoscope, or laparoscope technology.

In one embodiment of the invention, the fiber optic needle probe comprises a needle having a tip and a wall defining a bore. The needle is sized and shaped for nonintraluminal insertion into a specimen. At least a portion of an optical fiber is positioned within the bore of the needle. In a first embodiment, the optical fiber is independently movable within the needle. In a second embodiment, the optical fiber and needle comprise a single, integrated unit, i.e., the optical fiber is fixedly positioned within the needle and the needle and optical fiber move as one. A beam director is positioned in close juxtaposition to, the first end of the optical fiber to direct light from the optical fiber to the specimen being imaged. In a further embodiment of the invention, the wall of the needle comprises an optical port. In this embodiment of the invention, the beam director is positioned in close juxtaposition to the optical port and is capable or directing light and receiving light through the optical port. The port may be configured to permit transmission of light along a plurality of points substantially linear with a longitudinal axis of the needle. In another embodiment, the port is configured to permit transmission of light over a range of positions orthogonal to a longitudinal axis of the needle.

In another embodiment of the invention, the fiber optic needle probe needle comprises a coring tube positioned within the bore of the needle. In this embodiment of the invention, the optical fiber is positioned substantially within the coring tube (as used herein, "positioned substantially" means that greater than 50% of the length of the optical fiber is positioned within the coring tube). Optical elements comprising the beam director are positioned in close juxtaposition to the optical fiber and may be integral with the fiber or separate from the fiber.

In a further embodiment of the invention, the fiber optical needle probe comprises a two-channel needle assembly. The two-channel needle assembly comprises a first housing and a second housing defining a first and second channel, respectively. An optical fiber is positioned substantially within the lumen or channel of the second housing and is in optical communication with a beam director. The second housing is constructed of a rigid or semiflexible material capable of emitting a single mode optical beam and receiving backscattered or backreflected light from the sample. The second housing is positioned in close juxtaposition to the first housing and the entire assembly of the first housing and the second housing has a small outer diameter allowing the assembly to be inserted directly into tissues or specimens. The first and second housing are sized and shaped for nonintraluminal insertion into a specimen. In a further embodiment of the invention, the first housing comprises an extracting device (e.g., a cutting device, a coring device, an aspirating device or a pinching device). In one embodiment, the two-channel needle assembly is used as a biopsy needle with imaging capabilities.

The fiber optic needle probe can be used in conjunction with a number of different types of optical imaging systems, in particular, with systems which deliver and collect a single spatial mode optical beam. There are a variety of OCT imaging systems which are included within the scope of the invention, including those which provide optical path length scanning, tunable optical source scanning, optical source scanning, optical spectrum analysis imaging, and optical phase delay-line scanning. Other interferometric imaging and ranging techniques are also encompassed within the scope of the present invention. OCT is the preferred imaging technology to be used with the fiber optic needle probe described herein because it can perform very high sensitivity and high dynamic range measurements of the echo time delay and intensity of backreflected and backscattered light.

In the preferred embodiment of the invention, the fiber optic needle probe communicates with the imaging engine of an OCT device by means of a single mode optical fiber housed within the needle or, within the second housing, in the case of the two-channel needle assembly. In one embodiment, an actuating device is coupled to the fiber optic needle probe to effect the movement of any of the needle, the optical fiber, the beam director, and combinations thereof. The actuator allows an optical beam directed from an OCT device to be scanned by mechanically scanning the position and/or rotation of any, or all of, the needle, optical fiber, and beam director. In one embodiment of the invention, the actuator is a motor coupled to the wall of the needle and the motor comprises a motor and a coil, with at least one of the magnet and the coil capable of movement. In this embodiment of the invention, at least one of the magnet and the coil is coupled to the optical fiber and capable of causing a scanning motion of the fiber. Used in conjunction with an OCT imaging system, the fiber optic needle probes of the present invention enable the tomographic imaging of the micro-structure of internal organs and tissues which were previously impossible to image in a living subject.

The fiber optic needle probes of the present invention may be used in a variety of applications. In medical diagnostic and imaging applications the fiber optic needle probes may have a range of diameters and may be configured in the form of biopsy needles, hollow acupuncture needles, as part of cannulas, or the like. When the fiber optic needle probes of the present invention are used in conjunction with, or integrated with, biopsy devices, imaging of tissue or organs in proximity to the probe will guide the way the physician performs the biopsy and reduce sampling errors or injury to sensitive tissue structures. Similarly, the fiber optic needle probes of the present invention can be adapted for use in other surgical procedures, for example, in guiding the course of tumor resections.

However, the use of these fiber optic needle probes is not limited to medical diagnostic imaging applications in humans. In further embodiments of the invention, the probes are used for optical measurements (both imaging and nonimaging) in animals and plants. The fiber optic needle probes can also be used for applications which require spatially resolved spectroscopic analysis. In one such application, the fiber optic needle probe is used to deliver optical radiation to a tissue or organ system and to collect scattered radiation from the tissue or organ. Additionally, in another embodiment of the invention, the fiber optic needle probe is used to deliver optical radiation to a tissue, exciting fluorescence in the tissue. The fluorescent light produced by the tissue is then collected by the fiber optic needle probe. In a further embodiment of the invention, the fiber optic needle probes are used in process monitoring of chemical or material synthesis where the device characterizes inhomogeneities in the process using spectroscopic signatures.

BRIEF DESCRIPTION OF DRAWINGS

The foregoing and other objects, features, and advantages of the present invention, as well as the invention itself will be more fully understood from the following description of the preferred embodiments, when read together with the accompanying drawings, in which:

FIG. 1A shows a cross-section of FIG. 1B. FIG. 1B shows a perspective view of the needle housing. FIG. 1C shows a cross-section of FIG. 1D. FIG. 1D shows a perspective view of the needle housing.

FIG. 4A is a cross-section of FIG. 4B. FIG. 4B shows a perspective view.

FIGS. 5A and 5B show an embodiment of the invention where the wall of the needle comprises an optical port and the beam director is in close juxtaposition to the optical port. FIG. 5A is a cross-section of FIG. 5B. FIG. 5B shows a perspective view. FIGS. 5C and 5D show an embodiment of the invention where the housing of the needle has a variable diameter. FIG. 5C is a cross-section of FIG. 5D. FIG. 5D shows a perspective view.

FIGS. 10A and 10B show embodiments of the invention where the fiber optic needle probe comprises a two-channel needle assembly adapted for use as a core needle excisional biopsy device.

FIGS. 11B and 11C show enlarged views of the tip and end of the needle distal to the tip, respectively.

DETAILED DESCRIPTION OF THE INVENTION

Figure 1A:
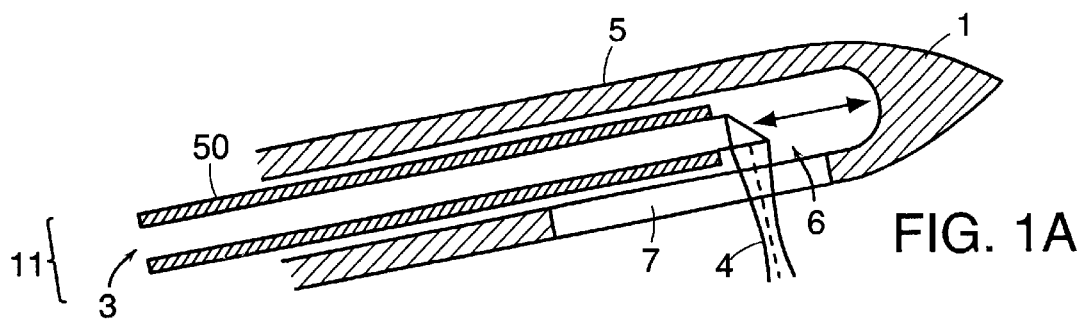
FIGS. 1A–D show embodiments of the invention where the needle housing has a wall which includes an optical port in the shape of an ellipse and the beam director is positioned within the bore defined by the needle.
Figure 1B:
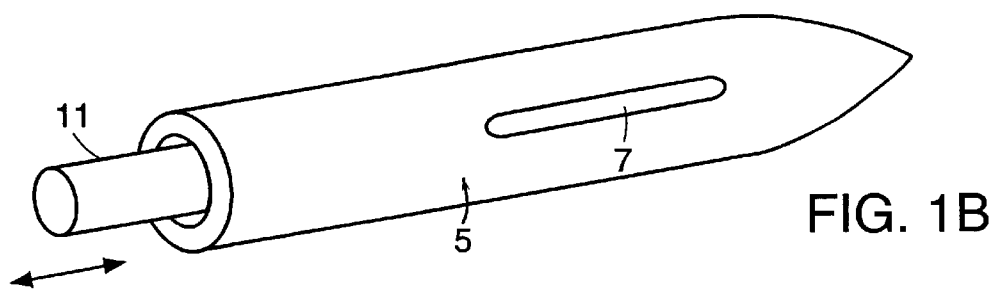
Figure 1C:
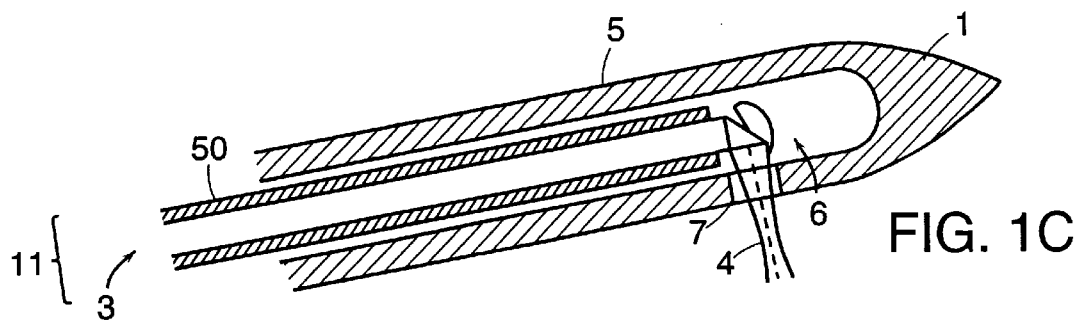
Figure 1D:
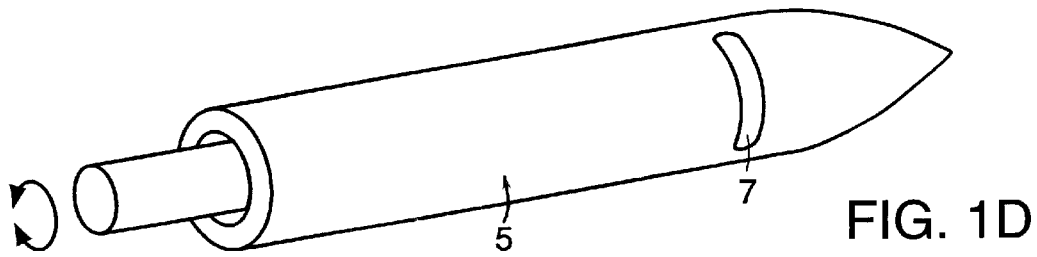

The invention comprises fiber optic needle probes for use with optical imaging systems to perform optical measurements of internal structures within a specimen. As used herein, the term "optical measurements" includes both imaging and non-imaging measurement. As used herein, the term "fiber optic needle probe" refers to a combination of a needle, an optical fiber, and a beam director. The term "specimen" as defined herein includes both biological and nonbiological specimens. Biological specimens typically refer to solid structures in a living organism such as tissues or organs or the walls of vessels. Examples of tissues include, but are not limited to, neural tissue, subcutaneous fat, connective tissue, cartilage, and muscle. Examples of organs which may be imaged include, but are not limited to, the heart, the liver, the lung, the brain, the kidneys, the ovaries, the prostate, the pancreas and skin. These specimens may be derived from humans, animals or plants. Nonbiological specimens include materials such mechanical assemblies or parts, and may include plastics, resins, polymers, composite materials, or the like.

I. Fiber Optic Needle Probe

A. Components

Needle Housing

The term "needle" 5 as defined herein refers to a housing conformed in the shape of a needle for piercing and probing materials, tissues or organs. As shown in FIGS. 1A–D, for example, the needle 5 may comprise a pointed end or sharp edge so long as it is able to pierce a material, tissue or organ with minimal trauma or damage to the material, tissue or organ. The needle 5 is constructed with a material which is rigid enough to be inserted into the desired material, tissue, or organ, but is also semiflexible and resistant to fracture. The needle 5 is sized and shaped for nonintraluminal insertion into a material tissue or organ. As used herein "nonintraluminal insertion" refers to insertion into a tissue, an organ, or through the wall of a vessel, which does not require insertion into an existing or created body opening or space. Preferred needle 5 materials include, but are not limited to, metal, plastic, and other polymers.

The needle 5 is typically small in diameter (generally less than about 5 mm, and preferably less than about 200 $\mu$m) yet large enough to accommodate the smallest diameter optical fiber 11 which can be fabricated to guide a single optical mode. In one embodiment of the invention, the needle 5 is fabricated to have a variable diameter and/or variable stiffness. Varying the diameter of the needle 5 permits the fabrication and use of longer length needles 5 than would be possible with a fixed diameter, thus extending the range of internal structures which can be measured or imaged and the accessibility of these structures to measurement or imaging. Varying the diameter of the needle 5 such that it increases from the distal end toward the proximal end, for example, produces increased rigidity near the proximal end, and increases the ability of the user to insert the needle 5 or guide it to the desired site of application. Variation may occur as a taper or in a step, or set of steps, in diameter. It is recognized that there are other techniques for fabricating a needle 5 with variable rigidity. These include, but are not limited to, varying the composition of the needle 5 or its microstructural construction. These implementations may result in a needle 5 with a constant outer diameter.

In another embodiment of the invention, the needle 5 further comprises a handle assembly. In a preferred embodiment of the invention, the fiber optic needle probe is held in a manner similar to a pencil and inserted into the biological tissue or material that is to be imaged. However, without loss of generality, it is also understood that the needle 5 can be held by other means. For example, in another embodiment of the invention, the needle 5 is mounted on a stereotactic frame which provides mechanical registration and precise positioning of the needle 5 relative to the object into which the fiber optic needle probe is being inserted. In a further embodiment, the needle 5 is mounted on the frame of a microscope or other viewing device which provides a magnified image of the surface of the object into which the needle 5 is being inserted. The needle 5 can also be inserted through the accessory port of a laparoscope and used for real-time imaging of solid organs during laparoscopic examination and surgery. In this case, the needle 5 housing will be significantly longer than in the embodiment where the needle 5 is part of a hand-held probe. In still another embodiment of the invention, the fiber optic needle probe is provided with connecting cables for connection to a variety of imaging systems and/or other actuating means.

The needle may be constructed using a transparent or semitransparent material in order to emit an optical light beam 4. Transparent materials include plastic, glass, and other polymers. In another embodiment of the invention, shown in FIGS. 1A–D, the needle 5 comprises an optical port 7. An optical port 7 as defined herein is an opening which may be covered or uncovered, including, but not limited to, a window, slot, keyhole or a transparent section in the wall of the needle 5. A transparent material may also cover the port 7 described above or span a section of the needle 5 such that it is integrated with the needle 5. As shown in FIGS. 1A–D, the optical fiber 11 emits light 4 through the optical port 7; and backscattered or backreflected 4 is received through the optical port 7 from the specimen being imaged. The optical port 7 must be large enough to permit transmission of the light beam 4 from the beam director 6 as the fiber 11 is scanned over its desired range of positions.

The optical port 7 may define an opening at the end of the needle 5 or along the side of the needle 5. When the optical port 7 is along the side of the needle, it may be configured in a variety of shapes including an oblong-shaped opening such as a slot. The major axis of the oblong may be parallel or perpendicular to the longitudinal axis of the needle 5. In one embodiment, the optical port 7 permits transmission of light 4 along a plurality of points substantially colinear with a longitudinal axis of the needle 5. In another embodiment, the optical port 7 permits transmission of light 4 over a range of positions orthogonal to a longitudinal axis of the needle 5. Other angular orientations of the oblong-shaped opening or slot with respect to the longitudinal axis of the needle 5 are also envisioned and encompassed within the scope of the present invention.

Optical Fiber (11)

At least a portion of an optical fiber 11 is positioned with a bore defined by the needle 5. Optical fiber 11 materials include glass, plastic, and other suitably optically transparent materials. In the preferred embodiment of the invention, the optical fiber 11 is a single mode optical fiber 11 which emits and collects a single, or nearly single, transverse mode optical beam 4 at, or near, its distal end. The fiber 11 consists of a core 2, usually cylindrical in profile, of elevated index of refraction (e.g., glass) surrounded by a cladding 3. The diameter of the core 2 depends upon the wavelength of the light that it is designed to carry as well as the optical properties of the core 2 and the cladding 3. For example, the diameter of the core 2 is generally in the range of 4 to 8 µm. Thus, the minimum diameter of the core 2 is a few optical wavelengths.

The cladding 3 of the fiber 11 should have a diameter large enough such that the electric field of the optical beam 4 or mode which is present in the cladding 3 is not substantially perturbed by the outer boundary of the cladding 3 so as to introduce appreciable loss or dispersion, since the optical beam 4 or mode in the core 2 decays in an exponential manner in the cladding 3 as a function of the distance away from the core 2. The cladding 3 surrounds the core 2 of the fiber 11 and the typical cladding 3 diameter in a fiber 11 used for optical communications is ~125–200 microns. However, it is understood that while the aforementioned are typical dimensions of the cladding 3, the cladding 3 can have a wide range of diameters and can be as small as 12–15 µm. Thus, extremely small optical fiber 11 diameters can be constructed which carry single mode optical beams 4. The smallest diameter cladding 3 for a single mode fiber 11 depends upon the operating wavelength and details of the fiber 11 construction, but in preferred embodiments of the invention the diameter of the cladding 3 will be in the range of 15 to 20 µm.

In a further embodiment of the invention, the optical fiber 11 is provided with a coating or jacket 50 surrounding the cladding 3, which can be a plastic, metal, polymer material, or the like. The jacket 50 of the fiber 11 does not serve to guide the optical beam 4 but acts to protect the fiber 11, strengthen it from breaking, and to increase its mechanical rigidity. In an embodiment of the invention where the fiber 11 is integrated with the needle 5, the needle 5 casing itself may serve as the jacket 50.

Beam Director (Distal Optical Element(s)) (6)

The optical fiber 11 is provided in close juxtaposition to a beam director 6 which serves to emit the optical beam 4 at an angle from the fiber 11 (usually approximately 90 degrees from the fiber 11 axis) to produce a focal spot of a desired spot size at a given distance from the fiber 11. Two parameters must be controlled by the beam director 6: (1) the focal length of the lens or other optical element that is used to focus the beam 4 emitted from the fiber 11, and (2) the effective distance of this lens or other optical element from the optical (mode) in the optical fiber 11. Light 4 which is backscattered or backreflected from the specimen is also collected by beam director 6 and directed back into the fiber 11.

In a one embodiment of the invention, the beam director 6 extends beyond the end of the needle 5 such that the optical beam 4 is transmitted around the end of the needle 5. Alternatively, as shown in FIGS. 1A–D, where the needle 5 comprises an optical port 7, the beam director 6 is positioned in close juxtaposition to the optical port 7 of the needle 5 such that it is capable of directing and receiving light beam 4 through the optical port 7. In a further embodiment of the invention, an orienting element is provided for maintaining the angular orientation of the fiber 11 and beam director 6 within the hollow needle 5 so that the beam 4 is transmitted in the desired direction.

As defined herein, a "beam director" 6 comprises optical element(s) provided at the distal end of the optical fiber 11 to deliver and to collect a single or nearly single transverse spatial mode optical beam 4. Any combination of focusing and beam directing elements 6 known in the art which have appropriate parameters of focal length and size may be used. The optical element(s) of the beam director 6 encompassed by the invention include, but are not limited to, a microprism, mirror (such as a fold mirror), lens, focusing element, and the like. In one embodiment of the invention, the optical fiber 11 includes an integrated lens at its tip and is in proximity to a right angle polished optically coated facet such that a focused optical beam 4 is emitted in a direction at an angle to the longitudinal axis of the fiber 11.

Figure 2A:
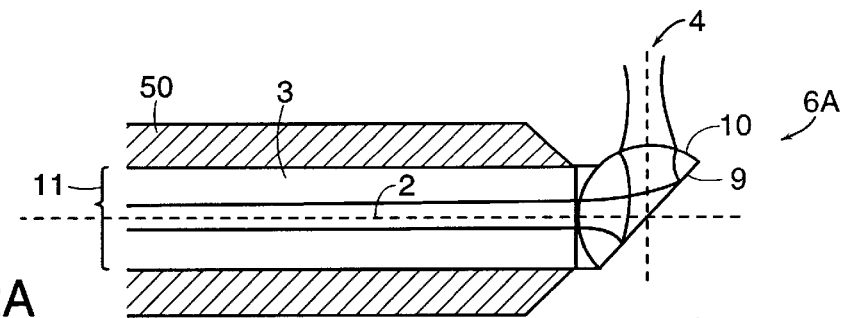
FIGS. 2A–E show views of optical fibers and beam directors in an embodiment of the invention where these are movable within the needle. The optical fibers and beam directors are shown in cross-section.
Figure 2B:
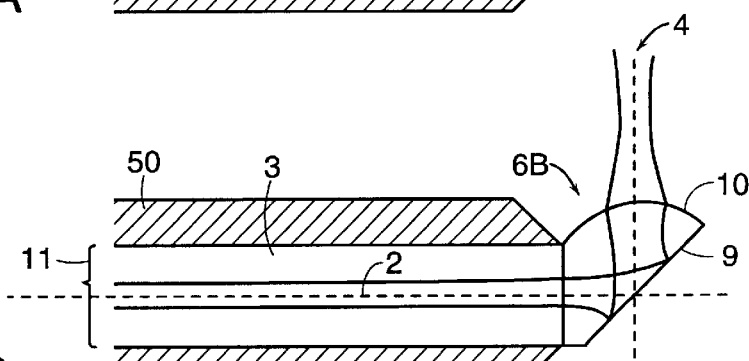

FIGS. 2A–D depict optical fibers 11 and beam directors 6 comprising different types of optical elements 6A, 6B, 6C, and 6D. FIGS. 2A–B show embodiments of the invention where beam director 6 is a ball lens. In these embodiments of the invention, the ball lens is ground or polished and coated with a high-reflective coating such that the optical beam 4 is internally reflected from the planar angled facet 9 and directed through the curved surface 10 of the ball lens. The refractive power of the lens is determined by the ball lens material, the size of the ball lens or its radius of curvature, and the index of refraction of the material into which the beam 4 is launched and which is in contact with the lens. The ball lens may be mounted directly on the end of the optical fiber 11 as shown in FIG. 2A (a section 6A of the ball lens is shown) or used with a spacer which controls its distance from the end of the fiber 11.

The focal spot size and focal position of the beam 4 may be controlled by changing the size of the ball lens and its spacing from the end of the fiber 11. The end of the fiber 11 may also be heat-treated in order to diffuse the boundary between the core 2 and cladding 3 region of the fiber 11. This causes the optical beam 4 within the fiber 11 to become unguided, at which point the beam 4 begins to diffract. The position where the core 2 is diffused away is controlled by controlling the point of application, temperature, and time of the heat treatment. This process is substantially equivalent to forming a spacer between the end of the fiber 11 and ball lens and is used as the second parameter in conjunction with the size of the ball lens to control the focused spot size and focal distance of the emitted beam 4.

FIG. 2B shows a second embodiment of the invention in which the beam director 6 is a ball lens which has been fabricated directly onto the fiber 11 by controlled melting of the fiber 11 (a cross section 6B is of this type of ball lens is shown in the Figure). Techniques for fabricating ball lens are well known in the art. The lens is ground and reflection-coated such that the optical beam 4 is directed at an angle from the fiber 11 axis and through the curved surface 10 of the lens. The effective position of the lens is controlled by heat-treating the end of the fiber 11 (at lower temperatures than those used to melt the fiber 11 and create the ball lens). The heattreating diffuses the boundary between the core 2 and cladding 3 of the fiber 11. In addition to the parameters discussed above, the process provides an additional way to control the focused spot size and distance of the emitted beam.

Figure 2C:
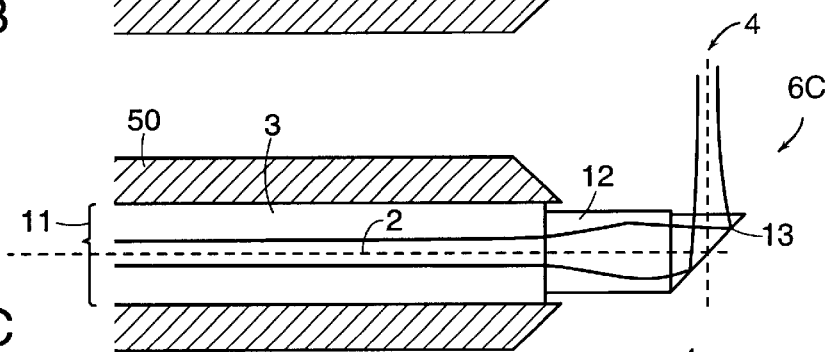

FIG. 2C shows another embodiment of the invention in which a beam director 6C is a graded index lens 12 with a microprism 13 on the end which is connected to the optical fiber 11. The microprism 13 deflects the beam 4 from the optical fiber 11 at an angle of approximately 90 degrees with respect to the longitudinal axis of the fiber optic needle probe. The angled facet forming the hypotenuse of the microprism 13 is optically coated such that it is highly reflecting at the wavelength of the light 4 that is being used. In this embodiment of the invention, the spot size of the focused beam 4 as well as the distance of the focus produced by this type of beam director 6 is controlled by controlling design parameters including the focal length (pitch) of the graded index lens 12, the spacing of the fiber 11 from the lens 12, and the distance from the lens 12 to the tissue or specimen (controlled in part by the size of the microprism 13). Once a desired focal length graded index lens 12 is chosen, the emitted beam 4 is focused by varying the distance between the fiber 11 end and the lens 12 and filling the gap between the fiber 11 end and lens 12 with an optically transparent cement. As noted previously, the end of the fiber 11 can also be heat-treated so that the boundary between the core 2 of the fiber 11 and the cladding 3 is diffused. This causes the core 2 of the fiber 11 to stop guiding the light 4 and the length of the fiber 11 treated behaves similarly to a spacer length.

Figure 2D:
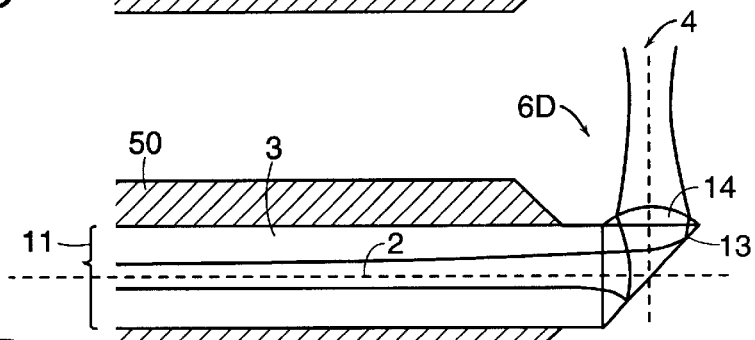

FIG. 2D shows another embodiment of the invention in which the beam director 6D is a microprism 13 connected to the optical fiber 11 such that the microprism 13 reflects the beam 4 emitted by the fiber 11 at an angle of approximately 90 degrees with respect to the longitudinal axis of the fiber 11/needle 5. A microlens 14 is connected to a second surface of the microprism 13 where the beam 4 exits such that the beam 4 is focused into the specimen. In this embodiment, the focal spot size of the beam 4 and the position of the focus is controlled by the focal length of the microlens 14 and the size of the microprism 13. In the foregoing embodiments, it is recognized that the microprism 13 may not be a right angle prism and that the beam 4 may be deflected at an angle which differs from 90 degrees from the longitudinal axis of the needle. In FIG. 2D, the microlens 14 is shown integrally attached to the microprism 13 and is made as a single unit. In another embodiment of the invention, the microlens 14 and microprism 13 are adjacent, but separate elements.

Figure 2E:
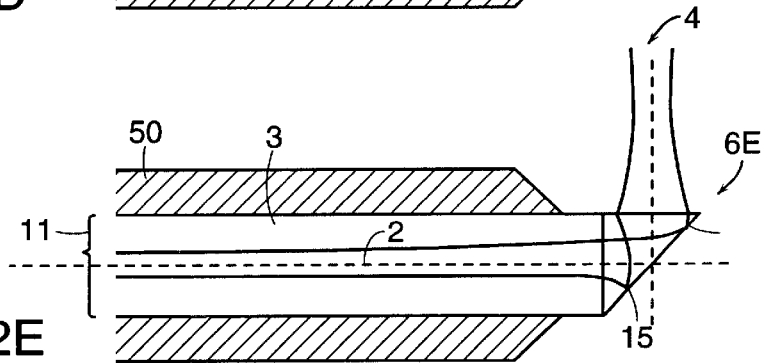

FIG. 2E shows another embodiment of the invention in which the beam director 6E is a focusing element 15 connected to an optical fiber 11 which performs focusing reflectively. In this embodiment, the optical fiber 11 is connected to a transparent element which has been formed into a reflective focusing element 15 such as an off-axis parabola. The reflective focusing element 15 is formed by the outer surface of the transparent material and a highly reflective coating. The optical beam 4 emitted from the optical fiber 11 begins to diverge at a designed distance from the reflective focusing element 15. After reflection, the beam 4 is reflected at an angle from the longitudinal axis of the fiber 11 and focused. The optical beam 4 is then emitted through a port 7, such as a window, in the transparent element. In this embodiment, the focal spot size of the beam 4 and the position of the focus is controlled by the orientation and curvature of the reflecting surface of the reflective focusing element and distance of the guiding section of the fiber 11.

In a further embodiment of the invention, a separate coreless fiber is attached between the optical fiber Hand the beam director 6. The coreless fiber allows the optical beam 4 to expand prior to being focused by the beam director 6. For example, given a standard single mode optical fiber 11 of 4.5 μm with a wavelength of 1300 nm, a coreless fiber with a length of ~800 μm will expand the beam to ~40 μm. A lens radius of curvature of ~225 μm will focus the light ~3 mm away to a spot of ~29 μm. The coreless fiber facilitates larger exit beam apertures and thus longer focal lengths, working distances, and depth-of-field. Beam directors 6 similar to those shown in FIGS. 2A, 2B, and 2D can be formed by mass transport lens technology, reflow-technology, using surface tension of UV glue, mechanical grinding or polishing, acid etching, and the like.

Although all the beam directors 6 shown in FIGS. 2A–E can have integral fold mirrors, in an additional embodiment of the invention, the fiber optic needle probe includes an "end-fire" lens integral to a single-mode fiber 11/coreless fiber unit. In a further embodiment, a separate 45-fold mirror is provided which is used to redirect light 4 directed from the fiber 11/lens unit. In many instances this is a preferred embodiment. Here, the fold mirror is attached to a fiber 11/lens unit. Methods of attachment include using heat shrink tubing or gluing the fiber 11/lens unit to the needle 5 wall.

It is recognized that for some applications, the optical element(s) comprising the beam director 6 will be shaped or covered with a shaped-structure so as to reduce contact of any sharp edges of the optical elements with the specimen, for example, a tissue. This serves the dual function of minimizing the drag on the needle 5 and also reduces trauma to the tissue as the needle 5 is moved. For other applications, the distal optical elements are shaped or covered with a shape having a sharp point to aid in insertion into the tissue or other type of specimen.

Finally, it is recognized that the aforementioned embodiments constitute only a limited number of examples of fiber distal optical elements. Any combination of a beam director 6 and focusing element, either integrated together, or combined separately, may be used, and are encompassed within the scope of the invention.

Actuating Device (30)

The optical fiber 11 and beam director 6 are moved using a mechanical actuator 30 so that they scan a desired pattern inside the biological tissue or material which is being imaged. As defined herein, an actuator 30 is any device which can control the position and/or orientation of the optical fiber 11, the needle 5, or both the optical fiber 11 and the needle 5. The actuator 30 can include, but is not limited to, a motor (such as a stepping motor), a DC or AC electromagnetic motor, a galvanometer, a piezoelectric actuator, electro-static deflector, pneumatic motor, MEMs devices, or other mechanical device which can control motion. In the embodiment of the invention where the fiber optic probe has a handle assembly, the actuator 30 may be either at the front or the back of the handle assembly. For some applications the actuator 30 assembly is initially separate from the needle 5 and fiber 11 such that the needle 5 is first introduced and the actuator 30 is attached to the fiber 11 and/or needle 5. Finally, in another embodiment of the invention, the actuator 30 is detached from the needle 5 and motion of the needle 5 is directed via a torque cable or other mechanical linkage.

In a further embodiment of the invention, position sensors are coupled to the fiber 11 and/or needle 5 to provide information as to the position of the fiber 11 and/or needle 5. This information is fed back to the control electronics of the actuators 30 which in turn adjust the position of the fiber 11 and/or needle 5. In some embodiments the window or port 7 contain fiducials, such as masks, which block the beam 4 from the optical fiber 11, to allow feedback information to be obtained from the distal end of the optical fiber 11.

In one embodiment of the invention, the movement of the beam director 6 is also controlled by the actuator 30. In the embodiment of the invention where the optical fiber 11 is actually attached to the beam director 6, several different types of movement can be controlled by the actuator 30. The fiber 11 and the beam director 6 may move as a unit independent of the needle 5 and housing and can be scanned in an axial or circumferential direction, or a combination of both. In this embodiment, the fiber 11 sits in the lumen of the needle 5 housing. In a further embodiment of the invention, the beam director 6 is attached to the needle 5 housing and the housing is continuously spun or scanned back and forth circumferentially. Alternatively, a beam director 6, such as a mirror, is moved independently of the optical fiber 11.

Figure 3:
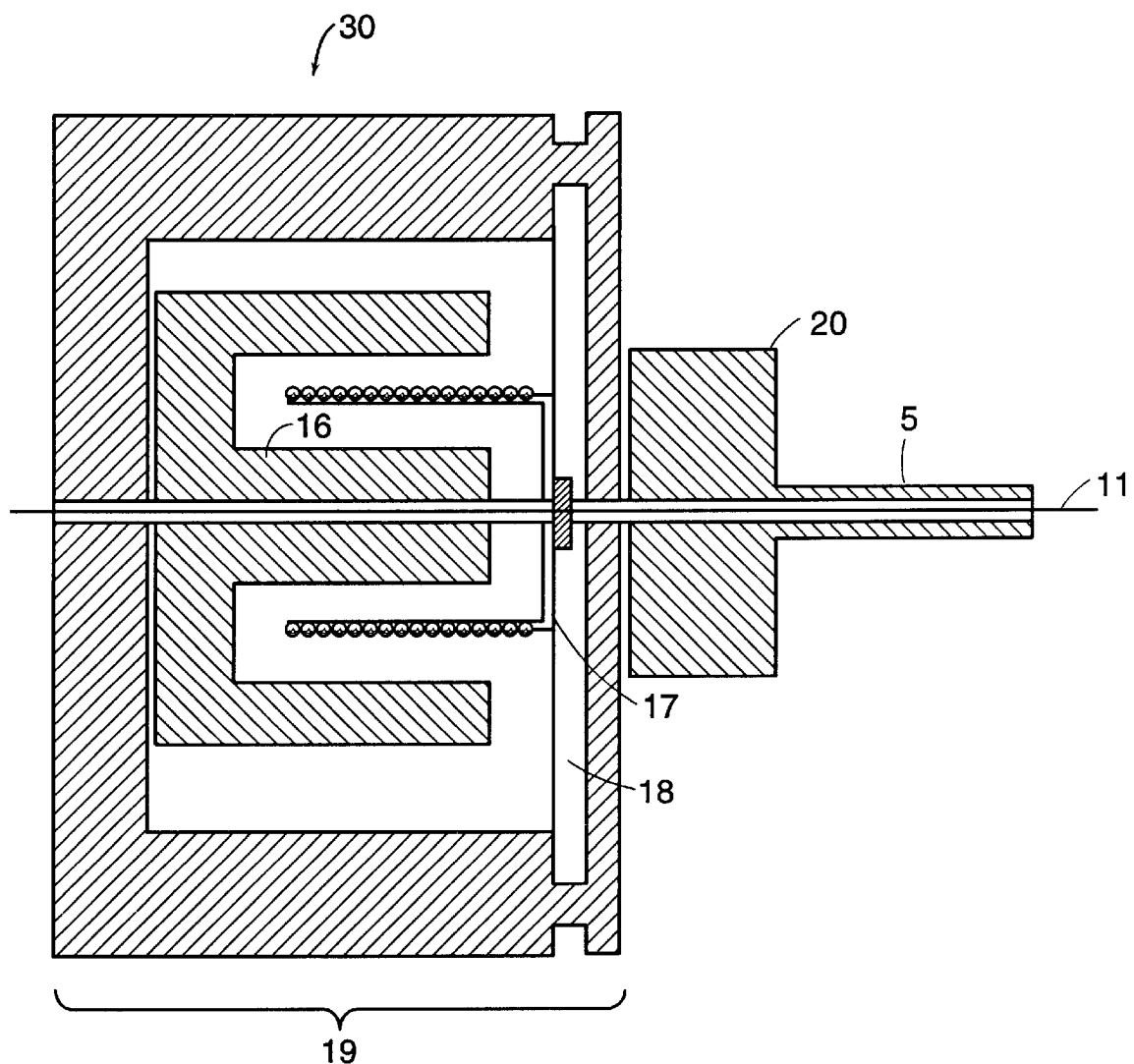
FIG. 3 shows an embodiment of the invention where the actuator is a DC servo motor and the needle housing, optical fiber, and motor, form an integrated unit.

In the embodiment of the invention where the optical fiber 11 and the beam director 6 are an integral or fixed part of the housing and the fiber 11, beam director 6, and needle 5 housing move as one, the actuator 30 is attached directly to the housing. In the embodiment where the optical fiber 11 and beam director 6 move within the needle 5 housing (i.e., independently of the needle 5 housing), the actuator 30 is directly attached to the optical fiber 11. In both cases a wide range of scanning options are possible. For example, in the embodiment shown in FIG. 3, to implement axial scanning in the case of an independent fiber 11/beam director 6 (not shown in the Figure) and needle housing 5, a simple DC servo motor (e.g., a speaker coil and position sensor) is directly seated onto the optical fiber 11. Here, the motor consists of a magnet 16 and a coil 17. In this embodiment, the coil 17 is housed on a flexure 18 to maintain proper registration and to allow smooth movement of the coil 17 in the axial direction and fixed registration in the lateral direction. In this embodiment, the magnet 16 and coil 17 have a small hollow center to allow the optical fiber 11 to thread through the center of the motor housing 19, magnet, 16 and coil 17 into a modified needle housing portion 20 which includes at its distal end the piercing portion of the needle 5. At least one of the magnet 16 and coil 17 is capable of movement. At least one of the magnet 16 and coil 17 is coupled to, or in mechanical communication with, the optical fiber 11. The optical fiber 11 can be secured to the magnet 16 or coil 17 using a variety of methods including simple epoxy. In one embodiment where the fiber optic needle probe is used as part of a biopsy device, the modified needle housing portion 20 forms part of a coring unit.

Other actuator 30/motor designs are also possible and included within the scope of the present invention. In a further embodiment of the invention, the motor is an offset motor with a mechanical pivot to multiply the stroke of the actuator 30 motor. A PZT motor or pneumatic actuator 30 may also be used, as well as all of the actuator 30 motor methods listed above. It should be clear to one of ordinary skill in the art that a variety of actuators 30 and motors might be used and that these may be attached to any, or all of, the fiber 11, beam director 6, and needle 5 housing to effect the movement of these elements.

Several different types of beam 4 scanning patterns are possible which are governed by the mechanical actuator 30. The optical beam 4 scanning patterns determine the type of measurement or image that will be generated. There are three parameters which will be used herein to describe the position and direction of the beam 4 emitted from the distal end of the fiber 11. These are defined with respect to the needle 5 axis. The coordinate oriented along the axis of the needle 5 is defined as "z". The angle "θ" defines the angular orientation of the emitted beam plane with respect to the x-axis ( i.e. θ=0 is along the x-axis). In cases where the optical beam 4 is not emitted at an angle 90 degrees from the axis of the needle 5, "φ" is used to designate the angle of emission from the needle 5 axis.

In one embodiment of the invention, the beam emission is scanned by varying the rotation of the optical fiber 11 and/or the needle 5. The scanning motion may be a continuous rotation of θ which generates a cross sectional image in a planar circular region oriented perpendicular to the needle 5 axis. Alternately, the scanning may be a reciprocally varying (i.e., forward and back) rotation of angle which scans some portion of a circle and generates a cross sectional image in a planar sector region oriented perpendicular to the longitudinal axis of the needle 5, the center of the said sector coincident with the needle 5. In the most general case, the angle φ of emission of the beam 4 may not be 90 degrees from the needle 5 axis. In this case the region which is scanned is a conical section or a sector like subset of a conical section. Finally, we note that in the case where there is a continuous angular scanning of the optical beam 4, it may be necessary to use an optical coupler on the optical fiber 11 between the fiber optic needle probe and the detection apparatus. This coupler permits continuous rotation of the fiber 11 while transmitting and receiving light from the fiber optic needle probe to the detection apparatus.

In another embodiment of the invention, the beam 4 is also scanned by varying the position of the beam 4 longitudinally (varying z). In this case the beam 4 position will be scanned in a reciprocal or periodic fashion (forward and back). The actuator 30 of FIG. 3 (i.e., motor comprising magnet 16 and coil 17) is particularly suitable for this scan motion.

Varying z generates a planar cross sectional image containing the axis of the needle 5. The orientation of the plane is determined by the orientation of the direction of the beam 4(angle θ). The orientation of the image plane is controlled by rotating the fiber optic needle probe along its axis, varying the angle θ. Finally, in the most general case, the angle φ of emission of the beam 4 is not 90 degrees from the needle 5 axis and the region which is imaged is described in terms of planar parallelogram which contains the axis of the needle 5.

In some of embodiments of the invention, orientations of the emitted beam 4 with φ not equal to 90 degrees are preferred such as when it is desired to image a region ahead of the needle 5. Another example where this orientation is desired is for Doppler flow applications where the needle 5 is inserted through the wall of a tissue into an artery. For Doppler flow measurements it is necessary to have the emitted and collect optical beam 4 oriented such that it is partially along (i.e., has some vector component along) the direction of flow such that the backscattered or backreflected light 4 will have a Doppler frequency shift because of the flow.

In further embodiments of the invention, in addition to simple single-parameter scan patterns, the position and orientation of the optical beam 4 is scanned in both the longitudinal z and angular θ directions. This provides measurements or image information on multiple cross-sections or volumetric three-dimensional information. The scan pattern is performed by scanning the angle θ and changing the longitudinal position z incrementally. This is an angle priority scan and corresponds to performing imaging in a series of circular planer cross-sections at different longitudinal positions. If the angle θ is not continuously scanned, but is scanned back and forth, this results in a imaging a series of sectors of circles at different longitudinal positions. Alternately, in another embodiment of the invention, the scan pattern will be performed by varying z rapidly (reciprocally) and varying θ is a longitudinal priority scan corresponding to scanning a series of planes parallel to the axis of the needle 5 at different θ angles. In still another embodiment of the invention, two parameters are scanned simultaneously. For example, the scan pattern may performed by varying θ continuously and rapidly and varying z slowly, corresponding to a corkscrew image plane. In all of these two-dimensional scanning patterns, the optical beam 4 is scanned over a three-dimensional volume. These scanning patterns can be used to generate three-dimensional measurements or images of an internal structure and construct volume renderings.

In some embodiments of the invention no scanning will be needed or desired. This, for example, would be the case in applications where a single parameter is measured or monitored over time. Changes of optical properties or flow (Doppler shift of the backscattered or backreflected light) are measured with the beam 4 along a single axis as other physical parameters in the tissue/specimen environment are varied.

In all of the aforementioned scanning geometries, it is understood that the cross-section being imaged is determined by a combination of the beam 4 scan geometry with the position and orientation of the fiber optic needle probe itself. The angular orientation and position of the tissue being imaged may also be changed by rotating the fiber optic needle probe. The insertion (in the z direction) of the fiber optic needle probe may also be changed. Finally, the entire position and orientation of the needle 5 may be controlled during the needle 5 insertion to guide it to the area of interest for imaging.

B. Fiber Optic Needle Probe Designs
Two-Piece Fiber Optic Needle Probe

In the embodiments shown in FIGS. 1A–D the bore of the needle 5 encases a movable optical fiber 11. The inside diameter of the bore is large enough to permit free motion of the fiber 11 and beam director 6 along the z direction and θ directions but not so large as to permit excessive wobble or position error of the fiber 11. The z position and θ angle of rotation of the fiber II and hence the z position and θ angle of the emitted and collected optical beam 4 are controlled by an actuator 30 or manual movement. In one embodiment of the invention, position sensors may be coupled to the fiber 11 or the actuator 30 to provide information as to the position of the fiber 11. In another embodiment of the invention, position information is fed back to control electronics of the actuator 30 to adjust the position of the optical fiber 11.

In one embodiment of the invention, the optical fiber 11 has sufficient rigidity so that z direction motion is actuated at the proximal end of the needle 5 with minimal backlash (see FIG. 1A). This z axis motion corresponds to alternately withdrawing and inserting the fiber 11 into the hollow needle 5 and results in a scanning of the z position of the emitted and collected optical beam 4. When the fiber 11 is actuated in the z direction, the fiber optic needle probe produces an image or measures the optical properties in a plane which contains axis of the fiber optic needle probe. In this case, the angular position θ of the emitted optical beam 4, and hence the angular orientation of the scanned plane may be controlled by rotating the entire fiber optic probe needle assembly. The angle of the beam 4 emission can be adjusted by using an index on the wall of the needle 5 or by the use of actuator(s) 30. The rotation of the entire needle 5/optical fiber 11 assembly may also be done manually by the operator holding the handle of the fiber optic needle probe. When precise control and indexing of the imaging plane and θ is required, rotation is performed by an actuator. Scanned angle θ motion of the fiber 11 and beam director 6 combined with controlled actuated changes in position z may be used to generated a three-dimensional scan pattern.

In a different embodiment of the invention (FIGS. 1C and 1D), the optical fiber 11 is actuated in the θ direction corresponding to varying angle of the optical beam 4 emitted and collected by the beam director 6 attached to the fiber 11. For this pattern of scanning, the fiber optic needle probe will produce an image or measure optical properties in a cross-sectional plane which is perpendicular to the longitudinal axis of the needle 5. In this case, the rotation of the optical fiber 11 is controlled by a mechanical actuator 30 at its proximal end. The rotational stiffness of the optical fiber 11 is large enough so that motion at the proximal end of the fiber 11 will be transmitted as a motion of the distal end of the fiber 11. The angular rotation of the optical fiber 11 is either continuous or reciprocal. Reciprocal angle scanning motion means that the angle of the beam 4 is scanned back and forth over a circle, or a subset of a circle, to generate a sector image. In this embodiment of the invention, the z position of the emitted optical beam 4, and hence the z position of the scanned plane, is also controlled by varying the insertion of the entire needle 5/fiber 11 assembly in the specimen (e.g., tissue or organ). In one embodiment of the invention, the insertion of the entire fiber optic needle probe is done manually by the operator holding the handle of the fiber optic needle probe. Alternately, when precise control and indexing of the imaging plane is required, the z position is varied by a mechanical actuator 30. Typically, the fiber optic needle z probe position will be varied by retracting or pulling back the fiber optic needle probe. In a preferred embodiment of the invention, the scanned angle θ motion of the fiber 11 and the distal optics of the beam director 6, combined with controlled actuated changes in position z, is used to generate a three-dimensional scan pattern.

Because the needle 5 is relatively short, the rotational stiffness of the optical fiber 11 is sufficient so that motion at the proximal end will be transmitted as a motion of the distal end of the fiber 11. However, torsion may be generated in the fiber 11 so that the distal angle position leads or lags behind the proximal angle position. Where extremely high image resolution is required, it may be necessary to measure or otherwise compensate for the distal fiber 11 position and emission angle of the beam 4 during scanning and correct for the angular lag.

Finally, we note that both the angle θ and the position z of the fiber 11 can be scanned simultaneously in an arbitrary pattern. In this case, means are provided for transmitting the optical beam 4 emitted from the beam director 6 which conforms to this scan pattern. In the case where the needle 5 is made from a transparent material, an arbitrary scan pattern can be implemented.

In another related embodiment (shown in FIGS. 4A–B), the optical fiber 11 and beam director 6 are housed in a modified hollow needle 21, which functions as both an introducer and an enclosure. In biological and medical applications, the introducer/enclosure 21 permits the entire assembly to be inserted into a solid biological tissue such as an organ or through a tissue wall into the lumen of a hollow biological organ/vessel. The inner diameter of the introducer/enclosure 21 is large enough to permit scanned motion of the fiber 11. In one embodiment, after the introducer/enclosure 21 is inserted into the tissue, the central fiber 11 and beam director 6 are advanced such that they protrude beyond the end of the introducer/enclosure 21 thus permitting the optical beam 4 to be directed into the tissue. Alternately, in another embodiment of the invention, the introducer/enclosure 21 is retracted slightly as the fiber 11 and beam director 6 are held in place, resulting in a net motion of the end of the introducer/enclosure 21 backwards such that the beam director 6 is exposed. The beam director 6 can thus be in full view of the tissue or other specimen that is being imaged. The preferred motion for scanning in this embodiment is scanning the fiber optic needle probe assembly such that the angle θ of the beam 4 is varied. However, it is also possible to actuate scanning by varying the z position of the fiber 11 and beam 4. The introducer/enclosure 21 covers part of the fiber 11 and reduces the friction that the tissue would have on the fiber 11 if it were in contact with the fiber 11. The beam director 6 in this embodiment is not covered by the introducer/enclosure 21 so the optical beam 4 can be transmitted into the tissue or other specimen into which the introducer/enclosure 21 has been inserted. In addition, since the area and volume of the distal optical elements comprising the beam director 6 are small, the amount of resistance to motion or drag produced by these elements is small and does not appreciably impede the scanning motion.

Figure 4A:
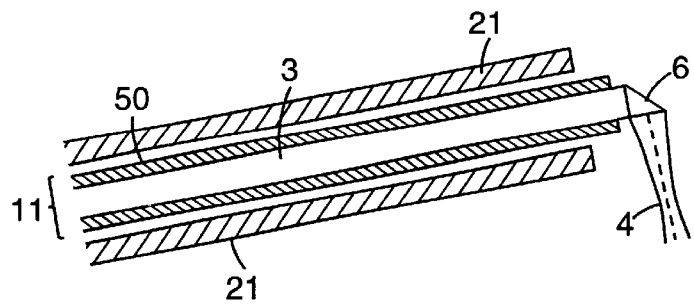
FIGS. 4A and 4B show embodiments of the invention where the needle is hollow and contains a movable optical fiber and beam director which may be advanced and retracted beyond the tip of the needle housing.
Figure 4B:
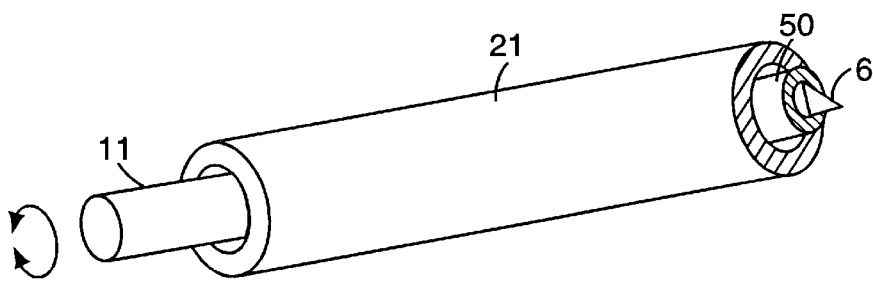

Finally although the schematic of FIGS. 4A and 4B show the use of a prism as a beam director 6, different implementations of beam directors 6 may be used. A preferred implementation for a medical application would be a covered beam director 6 or one having a rounded or smooth surface such that the trauma produced to the tissue from the scanning motion of the fiber 11 and distal optical elements of the beam director 6 would be minimized.

Integrated Fiber Optic Needle Probe

The integrated fiber optic needle probe design shown in FIGS. 5A–D permits the actuation of the fiber 11 and beam director 6 by actuating the needle 5 itself, such that the needle 5, fiber 11, and beam director 6 move as a single, integrated unit (i.e., the fiber 11 is fixedly positioned within the needle 5). In medical applications, the needle 5 moves relative to the tissue or other specimen into which it is inserted. This is contrasted with embodiments in which the fiber 11 and beam director 6 are actuated within a needle 5 or hollow tube and the needle 5 or hollow tube remains stationary with respect to the tissue or other specimen into which it is inserted.

The preferred scanning pattern when the fiber 11 is fixedly positioned within the needle 5 is scanning by rotating the fiber optic needle probe such that the angle θ of optical beam 4 emission is varied. This scan motion may be either continuous or reciprocal. Because the diameter of the needle 5 is small and its surface is smooth, the needle 5 may be rotated without significant friction or impediment to its motion. It is desirable that the distal end of the integrated fiber optic needle probe be as smooth as possible so that the rotary motion will not produce appreciable trauma to tissue. It is also recognized that the actuation or scanning of the integrated fiber optic needle probe is not restricted to angular motion and that other types of motion may be used depending on the particular application. For example, in medical imaging applications where image information over a three-dimensional volume is desired, the integrated fiber optic needle probe may be scanned with an angular motion either continuously or reciprocally and the entire needle 5 and fiber 11 assembly may be withdrawn or pulled back from the tissue. In some situations, as for example, when the fiber optic needle probe is being used to guide a biopsy procedure, the entire needle 5 and fiber 11 assembly may also be advanced into the tissue. This results in measurements or images being generated in a set of planes or nearly planer surfaces with varying longitudinal z positions.

Finally, in situations where there is negligible drag on the needle 5, for example, when imaging small holes in materials, or in other applications where the specimen being imaged retains its shape, such as in the imaging of mechanical assemblies, the integrated fiber optic needle probe is also scanned in the z direction. As noted previously, this scan pattern results in the measurements or images being performed in a plane which contains the longitudinal axis of the needle 5. In this case, rotation of the needle 5 and fiber 11 is used to select the angular orientation of the image plane.

In one embodiment of the integrated fiber optic needle probe design, the needle 5 material forms a jacket 50 around the optical fiber 11. Alternately, in another embodiment of the invention, the fiber optic needle is fabricated by inserting a conventional or custom-specification single mode optical fiber 11 into a hollow metallic or plastic tube and shaped like a needle 5 bonding the metallic or plastic tube such that the tube and the fiber 11 form an integrated unit. The needle 5 material must have sufficient thickness such that it has sufficient rigidity to permit insertion, guidance, and manipulation of the needle 5 and is resistant to fracture. The thickness of the needle 5 material, in conjunction with the minimum diameter of the cladding 3 of the optical fiber 11, will determine the minimum outer diameter of the integrated fiber optic needle device. The minimum thickness of the needle 5 material (and hence the thickness of the cladding 3 of the fiber 11) will depend strongly upon the properties of available materials and is expected to decrease if stronger, more flexible, materials are used for fabrication. The minimum thickness for the needle 5 material will be approximately 20 to 50 microns. This results in a minimum total outer diameter of the needle 5 of 100 to 200 microns.

Figure 5A:
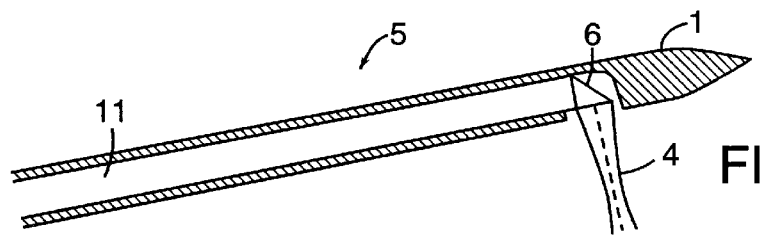
FIGS. 5A–D show embodiments of the invention where the needle and optical fiber form a single, integrated unit and the needle and optical fiber move together.
Figure 5B:
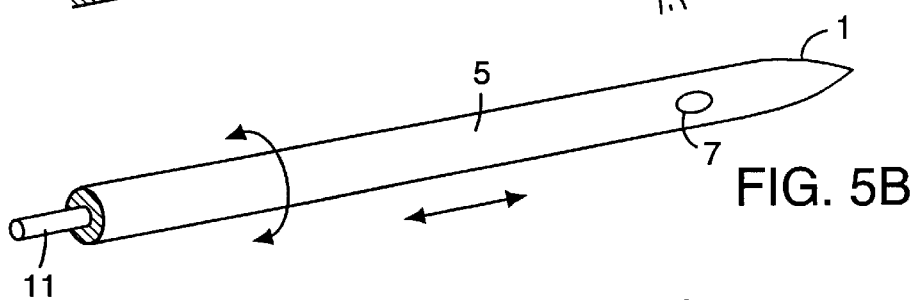
Figure 5C:
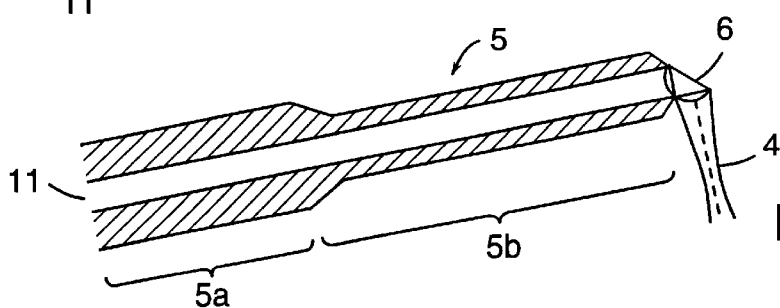
Figure 5D:
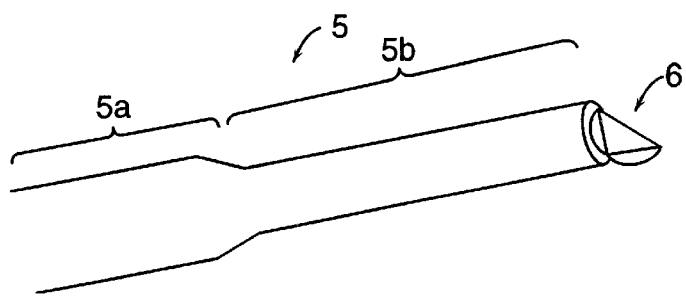

The integrated fiber optic needle probe design has a number of advantages. One important advantage of the integrated, single-piece fiber 11 and 5 unit is that it permits the fabrication of a needle 5 with a smaller outer diameter than in the embodiment in which the needle 5 is a hollow tube and the fiber 11 and beam director 6 are actuated or scanned within the needle 5. In the integrated fiber optic needle probe embodiment, such as shown in FIG. 5A, the single mode optical fiber 11 is contained within the needle 5. If the beam director 6 is encased by the needle 5, then means are provided for the optical beam 4 to be transmitted or passed through the needle 5. This is shown schematically in FIG. 5B. In this embodiment, the optical beam 4 is transmitted through an optical port 7 in the wall of the needle 5 and the beam director 6 is near, or at, the surface of the needle 5. It is also recognized that the fiber 11 and beam director 6 need not be encased within the needle 5 but may extend beyond the distal end of the needle 5 bore as shown in FIGS. 4B, 5C, and 5D. In this embodiment of the invention, the distal optical elements of the beam director 6 are in direct contact with the tissue, specimen, or other material into which the optical beam 4 is directed.

The integrated fiber optic needle probe design is also simpler than the two-piece fiber optic needle probe design in which the optical fiber 11 is actuated relative to the hollow needle 5 and hence may be less expensive to manufacture. Since this design does not require that the optical fiber 11 be actuated relative to a hollow needle 5, the outer diameter of the integrated fiber optic needle probe may be made smaller than in the two-piece design because there is no need to have a clearance space between the needle 5 and the optical fiber 11. For medical applications, the integrated fiber optic needle probe may have an extremely small outer diameter such that it may be inserted into living tissues internal to the body with minimal trauma. The small diameter of the integrated fiber optic needle probe permits it to be inserted through the walls of hollow organs or vessels and into the luminal spaces, or ducts, of these organs or vessels.

In the embodiments shown in FIGS. 5C and 5D, the diameter of the needle 5 is varied along its length such that a section 5a of the needle 5 is larger in diameter than another section 5b of the needle. This embodiment of the invention provides for increased rigidity at the wider section 5a of the needle 5.

Two-Channel Needle Assembly

In another embodiment of the invention, the fiber optical needle probe comprises a two-channel needle assembly (as shown in FIGS. 9A, 9B, 10A and 10B, for example). The two-channel needle assembly comprises a first housing and a second housing (details 43 and 44, respectively, in FIGS. 9A and 9B, and details 49 and 50, respectively, in FIGS. 10A and 10B). The first and second housing define a first and second channel, respectively. The term channel as used herein refers to a lumen within the housings. The optical fiber 11 is substantially positioned within the channel of the second housing. The second housing may be a rigid or semiflexible material, and is capable of emitting and collecting a single mode optical beam 4. The second housing 44 is in close juxtaposition to the first housing 43 and the entire assembly has a small enough diameter to allow it to be inserted as a unit directly into tissues or other specimens to permit nonintraluminal insertion into the tissue or specimen. In this embodiment of the invention, the actuator 30 is in communication with at least one of the first housing 43, second housing 44, optical fiber 11, and beam director 6, and is capable of moving at least one of the second housing, optical fiber 11, and beam director 6, so as to scan the internal structure of a specimen. In a further embodiment of the invention, the first housing comprises an extracting device which may be a cutting device (for example, a sharp edge formed by the wall of the first housing itself or a movable cutter positioned within the lumen of the first housing) and the two-channel needle assembly is used as a biopsy needle with imaging capabilities. In further embodiments of the invention, the extracting device may be an aspirating or pinching device.

II Optical Imaging with the Fiber Optic Needle Probe

A. Optical Imaging Engine

The fiber optic needle probe is designed for use in conjunction with any optical imaging engine which requires the controlled delivery and collection of a single spatial mode optical beam. The imaging engine includes the associated sub-systems such as optics, electronics, motors, computers, and controls necessary to generate high resolution images, control image acquisition, or otherwise, process, quantitate, and display images. Although the fiber optic needle probe of the present invention can be integrated with OCT, it is also understood that cross-sectional images can be measured using any technique which is capable of performing a high resolution, high sensitivity measurement of the echo time delay, coherence properties, frequency properties, or other properties, of backreflected or backscattered light signals. These techniques include, but are not limited to, nonlinear cross-correlation techniques which measure the time variation and intensity of light. It is understood that this invention can be applied with any optical measurement diagnostic technique (i.e., both imaging and nonimaging) which requires the delivery of a single transverse mode optical beam and the collection of reflected, remitted, or backscattered light in a single spatial optical mode where the position or orientation of the optical beam is scanned in a controlled pattern. These include imaging modalities such as other interferometric and noninterferometric imaging systems, fluorescence and other spectroscopic imaging systems, Raman imaging, single photon confocal imaging, multiphoton confocal imaging systems, and combinations thereof. It is also understood that the fiber optic needle probe may be used in a nonimaging modality where it is desired to perform optical measurements of internal body structures on a microstructural scale, but where data may be represented in a form other than an image.

OCT Imaging System

Figure 6:
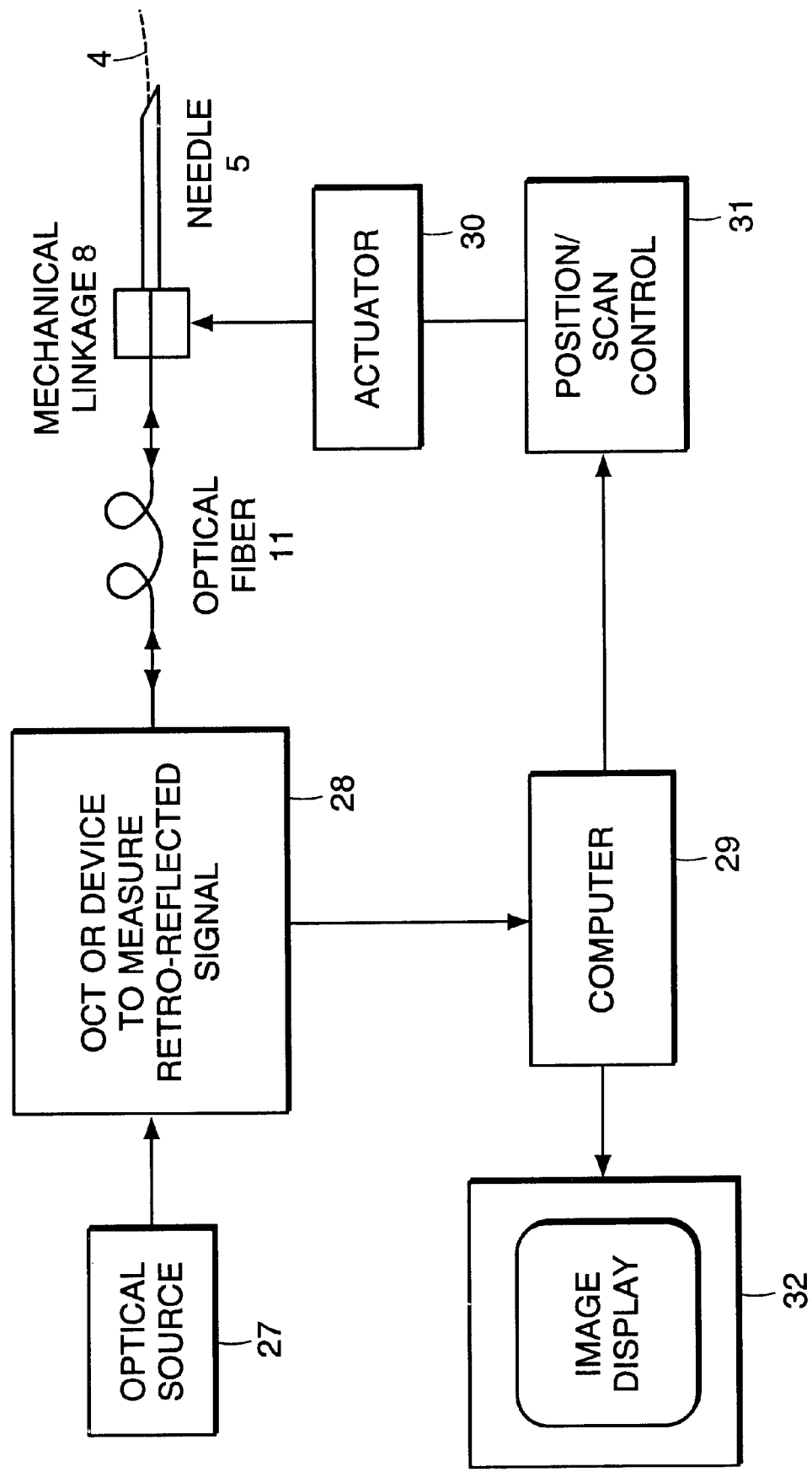
FIG. 6 shows an embodiment of the invention where the fiber optic needle probe is used in conjunction with an OCT imaging system.

FIG. 6 shows a schematic containing the principle system modules in an OCT imaging system used with the fiber optic needle probe in a preferred embodiment of the invention. The system includes the fiber optic needle probe module which consists of a needle 5, optical fiber 11, and mechanical linkage 8. Light is coupled from an optical source 27 to the optical fiber 11 in the needle 5 and directed into the tissue or other specimen which is to be measured or imaged. An OCT measurement apparatus 28 performs high sensitivity, high precision measurements of echo time delay (distance) and magnitude of the backscattered or backreflected light through the optical fiber 11. The resulting data is recorded by a computer 29, or alternatively, may be used to generate a video signal such as NTSC or PAL signal and the data directly displayed on a TV monitor. A mechanical actuator 30 is attached to the optical fiber 11 and/or needle 5 and is used to scan the fiber 11, or the needle 5 and the fiber 11 in the integrated fiber optic probe embodiment. In the case where the optical fiber 11 and/or needle 5 are continuously rotated to scan the optical beam 4 with a varying emission angle, the mechanical linkage 8 provides a rotating optical coupling. This couples light from the rotating distal end of the optical fiber 11 connected to the needle 5 to the stationary proximal end of the fiber 11 connected to the measuring apparatus. The mechanical actuator 30 which is connected to the fiber 11 is driven by a position- and scan-controller 31 in order to scan the optical beam 4 emitted by the fiber 11 optic needle probe in the desired pattern. The computer 29 controls and/or measures the scan pattern of the optical beam 4 and measures the backreflected or backscattered signal profile as a function of the scan pattern. The computer processes this information and represents it as an image on a display module 32. The imaging information may also be synthesized into a video NTSC or PAL) format and displayed on a screen or recorded on high resolution (SVHS or equivalent) video tape. Since in many cases the image resolution may be higher than standard video, digital video storage and display techniques may also be used.

There are several different embodiments of OCT imaging engines including: (1) embodiments which use a low coherence light source and an interferometer in conjunction with methods which scan the group and phase delays of light in a reference arm or shift the frequency of light in a reference arm; (2) embodiments which use a low coherence source, an interferometer, and an optical spectrum analyzer to analyze the output spectrum of the interferometer; and (3) embodiments which use a narrow linewidth frequency tunable optical source and interferometer. In addition there are other systems which use non-interferometric methods to measure the echo time delay of backscattered or backreflected light. It is also understood that the application of the fiber optic needle probe is not limited to OCT imaging.

The OCT measurement module 28 (or other measurement module), as well as the position and scan controller 31, are controlled by a control computer module 29 which is responsible for synchronization, generating drive waveforms, generating necessary trigger pulses, storing and recalling data, and performing any necessary signal and image processing. The control computer module 29 may also function as part of the display module 32. The display module 32 receives data from the computer module 29 and/or directly from the OCT measurement module 28.

Visualization may be performed with an OCT display module 32 (e.g., an image module) and/or a standard video monitor and/or a CRT. In medical imaging applications, the OCT images may be displayed simultaneously with, or merged with, other imaging modalities such as ultrasound or MRI to permit real-time guidance and placement of the fiber optic needle probe. In addition to the information provided by the OCT imaging system, such visualization techniques will permit other critical data to be analyzed, for example, permitting retrieval of previously acquired images and access to patient records while the procedure is being performed. Finally, since OCT images are extremely high resolution and will typically exceed the resolution of conventional video, they may be stored in digital form.

III. Applications for Imaging Internal Body Structures

For medical applications, the operator inserts the fiber optic needle probe into the tissue being imaged. In one embodiment of the invention, the imaging process is ongoing during the insertion procedure, in which case this image information is used to guide the insertion of the fiber optic needle probe and its placement. In a further embodiment of the invention, fiber optic needle probe insertion and placement is guided using external features and landmarks of the body and known anatomy. Insertion and placement may also be guided based on data from other medical diagnostic modalities such as X-ray, computed tomography, ultrasound, magnetic resonance imaging, and the like. Where applicable, other forms of imaging including microscopic, laparoscopic, or endoscopic visualization; ultrasound, magnetic resonance imaging, radiography or computed tomography may be performed prior to, or in real-time, during the fiber optic needle probe insertion, to guide the fiber optic needle probe insertion and placement.

For most medical applications the needle 5 will be inserted into tissue or through tissue into a hollow sinus or intraluminal space. In its most common application, it is envisioned that the fiber optic needle probe will be inserted from a position exterior to the body, e.g., through the skin, subcutaneous fat, and muscle layers into the body as the needle 5 is sized and shaped to permit nonintraluminal insertion. However, in other embodiments of the invention, the fiber optic needle probe is also be inserted through a tissue from a position inside the lumen of a hollow organ or from an interior position in the body that may be exposed through an open field surgical procedure or laparoscopy.

The upper limit on the length of the needle 5 will be constrained by the need to guide the fiber optic needle probe during insertion and scan it during optical measurement (either nonimaging or imaging). The needle 5 should be long enough for the distal end of the needle 5 to extend into a region of interest in the body upon insertion. If the fiber optic needle probe is inserted into tissue, through the skin, or through an organ barrier in order to obtain measurements or images of a solid tissue structure, then the length of the needle 5 may range from a few millimeters to as long as several centimeters. If the fiber optic needle probe is inserted through tissue into a hollow organ or lumen, then the length of the needle 5 may be longer than in the case where the fiber optic needle probe is inserted into a solid tissue without a lumen. In the case where the fiber optic needle probe is inserted through a tissue wall and used in a luminal space, the luminal space is used to guide the fiber optic needle probe to the point at which nonimaging measurements or imaging measurements are to be performed. Since the mechanical drag or friction on the needle 5 used in a luminal space is less than in the case where the fiber optic needle probe is inserted into a solid tissue, a longer needle 5 may be used in this scenario. The preferred length of the needle 5 can be optimized to accommodate a specific application.

The cross-section over which the fiber optic needle probe performs imaging is determined by the scanning pattern of the optical beam 4 that the fiber optic needle probe delivers and collects. The optical scan plane may be either along the longitudinal axis of the needle 5 or perpendicular to the longitudinal axis of the needle 5. The scan pattern may also result in a surface of illumination which may take on a complex form such as cone, sector of a circle, helical surface, etc. The position and orientation of the optical scan plane is controlled by the motion of the optical fiber 11 and beam director 6 which deliver and collect the optical beam 4. As previously discussed, in the two-piece fiber optic needle probe embodiment where the fiber 11 and beam director 6 are housed in a hollow needle 5, and the fiber 11 can move within the needle 5, the optical fiber 11 and beam director 6 are scanned relative to the hollow needle 5 housing. Alternatively, in the integrated fiber optic needle probe embodiment where the fiber 11, beam director 6, and needle 5 form single, integrated unit needle 5, the position and/or orientation of the needle 5 itself is scanned (the movement of the fiber 11 being dependent on the movement of the needle 5). In both embodiments, the overall position of the fiber optic needle probe is optimized as the fiber optic needle probe is inserted, or manipulated, during imaging to determine the orientation of the cross-sectional planes as well as to select what structure will be imaged.

Figure 7A:
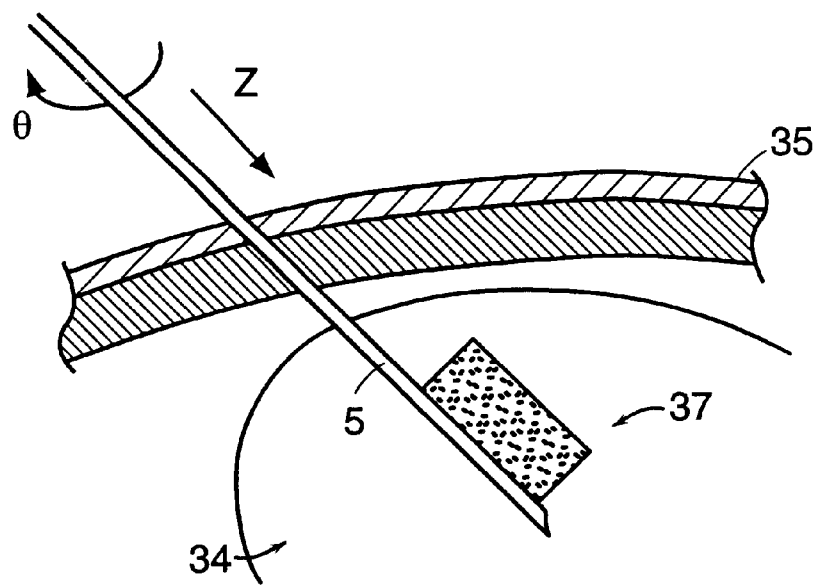
FIGS. 7A–D show embodiments where the fiber optic needle probe is used in internal body or intraluminal imaging applications.
Figure 7B:
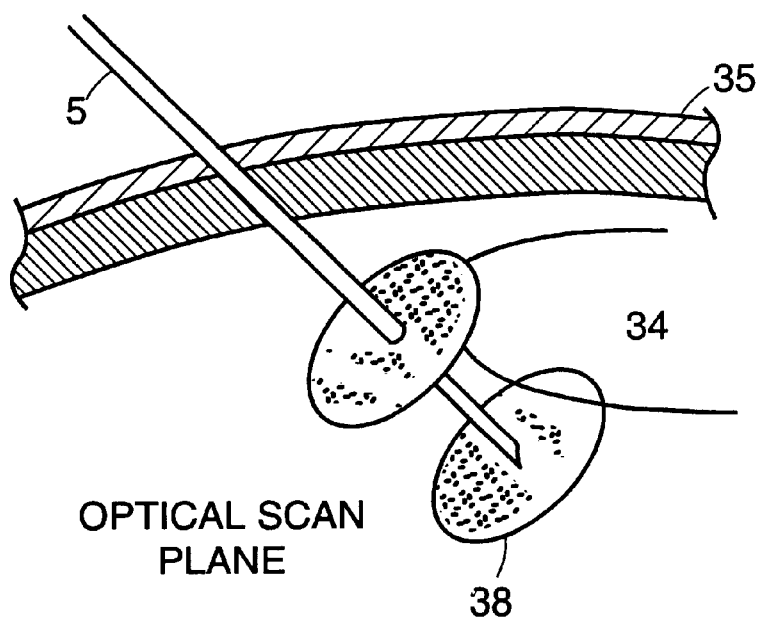

FIGS. 7A–D show embodiments of the invention where the fiber optic needle probe is used for internal body imaging such as in medical applications. In an embodiment of the invention shown in FIG. 7A, a fiber optic needle probe is inserted into a solid organ 34 and used to image the internal structure of the solid organ 34. The organ structure which can be imaged safely will depend on the diameter of the needle 5 and its sensitivity to trauma from the needle 5 insertion and manipulation. It is envisioned that different diameter and length needles 5 will be used depending on the application. In some applications, the fiber optic needle probe is inserted into a space or sinus within the body and imaging is performed across the boundary of an organ into its interior (as shown in FIG. 7B). In a further embodiment of the invention, imaging is performed across the boundary of a tumor for the purposes of localizing the border of the tumor.

Figure 7C:
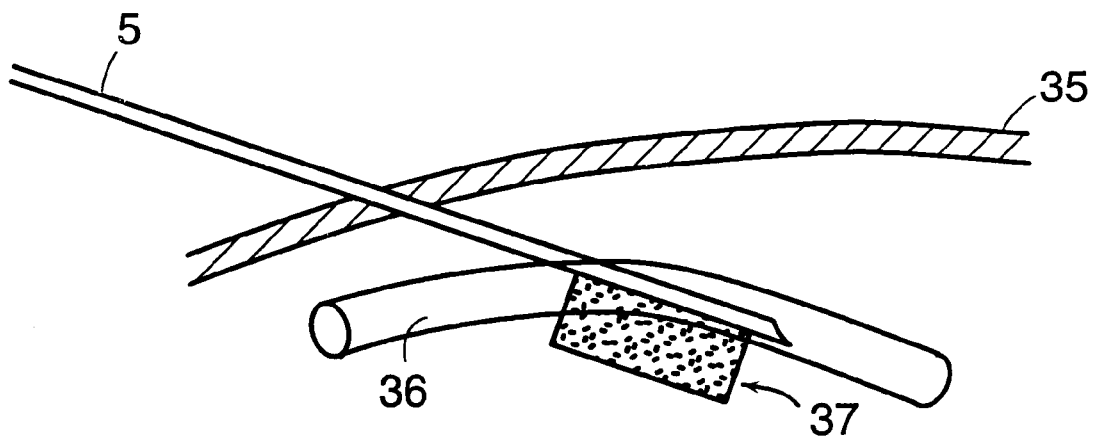
Figure 7D:
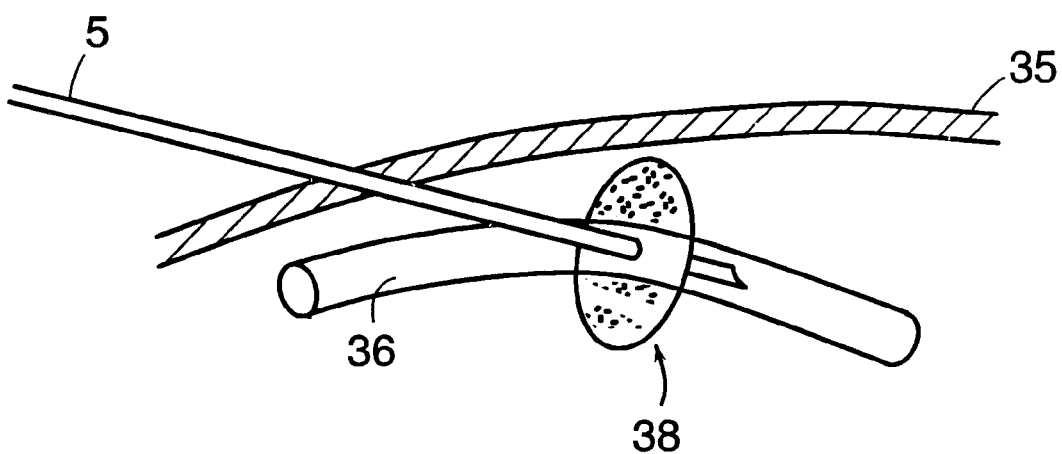

In the embodiment of the invention shown in FIGS. 7C and 7D, the fiber optic needle probe is inserted from an exterior or interior part of the body through intervening tissue 35 into a hollow organ or lumen structure 36. Lumen structures 36 may include blood vessels such as veins or arteries, or other luminal or ductal structures. The fiber optic needle probe may be used to perform cross-sectional imaging either perpendicular to the longitudinal axis of the needle 5 across the lumen structure 36, or along the plane of the needle 5 across the lumen structure 36. It is also understood that imaging may be performed by the fiber optic needle probe, for the process of inserting the fiber optic needle probe with the purpose of guiding said insertion.

For purposes of illustration, imaging is shown as being performed in a plane 37 containing the needle 5 in FIGS. 7A and 7C, and in a plane 38 perpendicular to the longitudinal axis of needle in FIGS. 7B and 7D. The image planes 37 and 38 are shown as shaded regions in the Figures. The depth of the region which can be imaged (as measured from the needle 5) is determined by the intensity of the light 4 which is emitted from the fiber optic needle probe, by the attenuation of the backreflected of backscattered light 4 which is collected by the fiber optic needle probe, by the sensitivity of the measurement apparatus, and by the desired rate of scanning and image acquisition time. Typical imaging depths in most biological tissues are 2–3 mm, therefore image information can be obtained from cross-sectional planes of surfaces within a cylinder of approximately 4 to 6 mm diameter. Imaging parameters and the performance of the imaging system are dependent on the details of the measurement apparatus as well as the properties of the tissue or specimen being measured or imaged, and should be optimized appropriately.

Stylette and Cannula

Figure 8A:
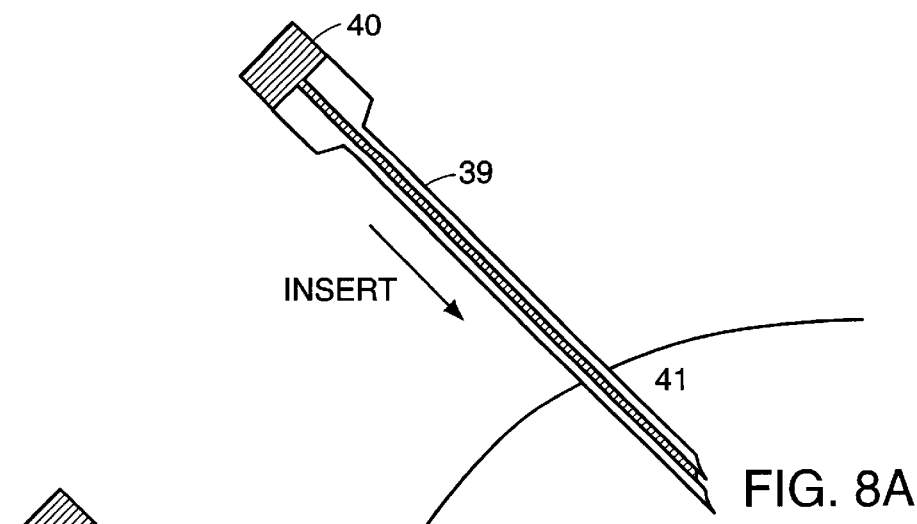
FIGS. 8A–8C show an embodiment of the invention where a solid tissue or organ is imaged using a stylette and a soft or semiflexible cannula with an integrated fiber optic needle probe in a multistep operation.
Figure 8B:
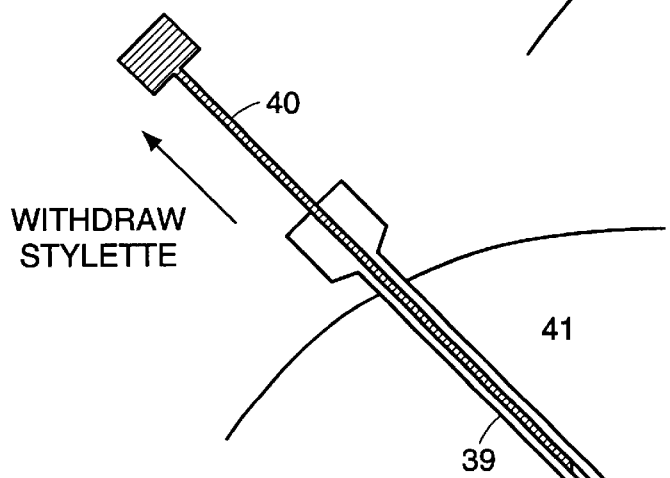
Figure 8C:
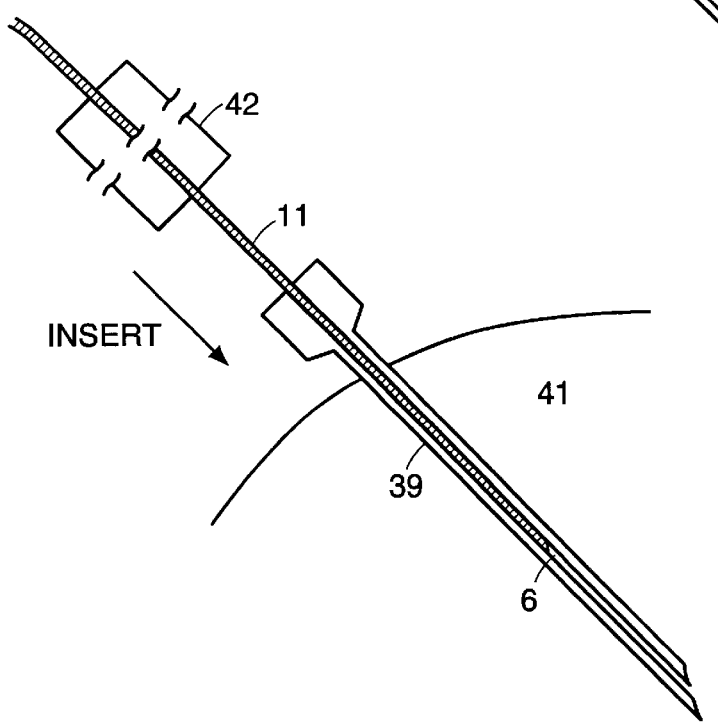

In a further embodiment of the invention, an optical fiber 11 is inserted into an object to be imaged with the aid of a stylette 40 and cannula 39 as shown in FIGS. 8A–C. This method of insertion entails providing a hollow tube which functions as a cannula 39. The cannula 39 has a wire stylette 40 or equivalent rigid structure inside which serves to increase the mechanical rigidity of the cannula 39 during the insertion process. The stylette 40 may extend beyond the cannula 39 if the cannula 39 is open at the distal end and the stylette 40 may have a sharpened point to facilitate introduction into the tissue 41. The cannula 39 may also be closed at the distal end in which case the stylette 40 extends up to the distal end and is encased by the cannula 39. In one embodiment, the cannula 39 is at least partially transparent.

The stylette 40 and cannula 39 are inserted or introduced together and guided such the distal end of the cannula 39 is in the structure which is to be measured or imaged. After insertion, the stylette 40 is withdrawn, leaving the hollow cannula 39 in place. As shown in FIG. 8C, an optical fiber 11 and beam director 6 is then inserted into the hollow cannula 39.

In the embodiment of the invention where the cannula 39 is transparent, then fiber 11 and beam director 6 are inserted such that the beam director 6 emits and collects the optical beam 4 through the cannula 39. This embodiment has the advantage that the fiber 11 and beam director 6 may be scanned in an arbitrary pattern because there is no impediment to the transmission of the optical beam 4 into the tissue or specimen.

In the embodiment of the invention where the cannula 39 is open at the end, then the optical fiber 11 and beam director 6 are inserted such that the beam director 6 extends beyond the end of the cannula 39 and thus emits the optical beam 4 directly into the tissue or specimen and collects the optical beam directly from the tissue or specimen. In this case, the cannula 39 need not be made of a transparent material. This embodiment is similar to the hollow needle 5 introducer/ enclosure embodiment shown in FIGS. 4A–B and discussed previously. The stylette 40 and cannula 39 may be considered an extension of the hollow needle 5 introducer/ enclosure where the hollow needle 5 introducer/enclosure (e.g., cannula 39) provides a hollow flexible sleeve which is itself introduced by the aid of a stylette 40.

After insertion, the optical fiber 11 and beam director 6 are mechanically actuated so that the optical beam 4 is scanned in the desired pattern. In one embodiment of the invention, the cannula 39 or the actuator 30 is already connected to the fiber 11 during the insertion process. Alternatively, in another embodiment of the invention, the actuator is attached by a clamp or chuck 42 to the fiber 11 after it is inserted, to make the insertion of the fiber 11 easier and more convenient.

In a further embodiment of the invention, the stylette 40 and cannula 39 are used in conjunction with an integrated fiber optic needle probe. In this embodiment, the stylette 40 and cannula 39 are inserted into a tissue or other specimen, the stylette 40 is withdrawn, and the integrated fiber optic needle probe is then inserted into the cannula 39. The presence of the cannula 39 serves to reduce the amount of drag or friction from the tissue or other specimen on the fiber optic needle probe when the probe is mechanically actuated. In this embodiment of the invention, the cannula 39 also serves to protect fiber optic needle probe from excessive bending or stress at the surface of the tissue or other specimen where such bending or stress may be more severe.

Biopsy Needle

In a further embodiment of the invention, image information from the fiber optic needle probe of the present invention is used to guide and/or place a conventional excisional biopsy procedure. The fiber optic needle probe may be used in conjunction with, or integrated with, a standard biopsy instrument such as a fine needle aspirator, or core biopsy needle, to identify the position of the instrument with respect to the surrounding tissue structure. Conventional excisional biopsy instruments have large diameters and the tissue removal process can produce significant tissue trauma. Unnecessary biopsies and sampling errors can be reduced by using the fiber optic needle probe to identify abnormal tissue or to avoid biopsy near sensitive structures such as blood vessels or nerves. In the present invention, the biopsy device can be used separately from the fiber optic needle probe or integrated together with the fiber optic needle probe. For example, if the biopsy device has a large diameter, it may pass over the fiber optic needle probe. Alternately, the fiber optic needle probe may have an additional channel built into it which permits the aspiration of tissue from its distal end, as in the two-channel needle assembly embodiment.

Integration with a Fine Needle Aspiration Device

In one embodiment of the invention the fiber optic needle probe comprises a fine needle aspiration device. In this embodiment, the fine needle aspiration device consists of a hollow biopsy needle which is inserted into tissue and used to aspirate tissue into the needle by applying calibrated suction on the proximal end of the biopsy needle. The needle diameters used in a fine needle aspiration device are typically 1 mm and are typically larger than the diameter of the fiber optic needle probe. Because of this, the fiber optic needle probe may be configured as a fine needle aspiration biopsy device without significantly increasing its size or impairing its function. The purpose of providing a fiber optic needle probe imaging device comprising a needle biopsy device is to allow imaging of a tissue near a biopsy site.

Figure 9A:
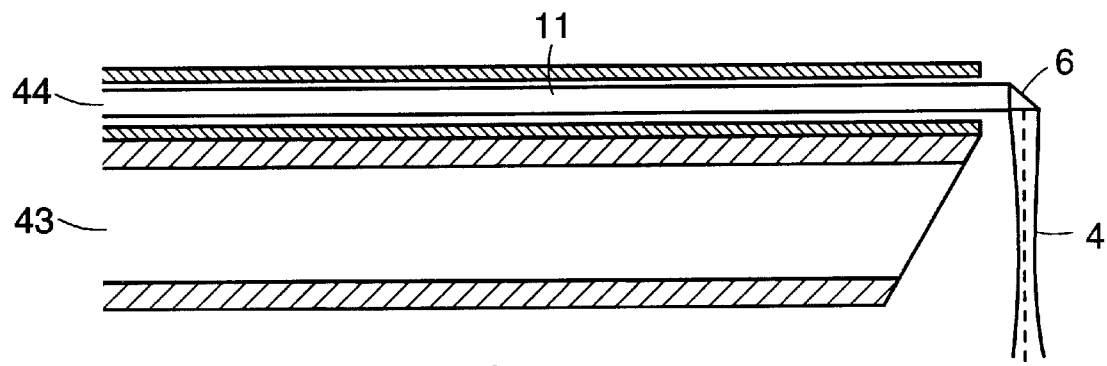
FIGS. 9A and 9B show embodiments of the invention where the fiber optic needle probe comprises a two-channel needle assembly adapted for use as a fine needle aspiration excisional biopsy device.
Figure 9B:
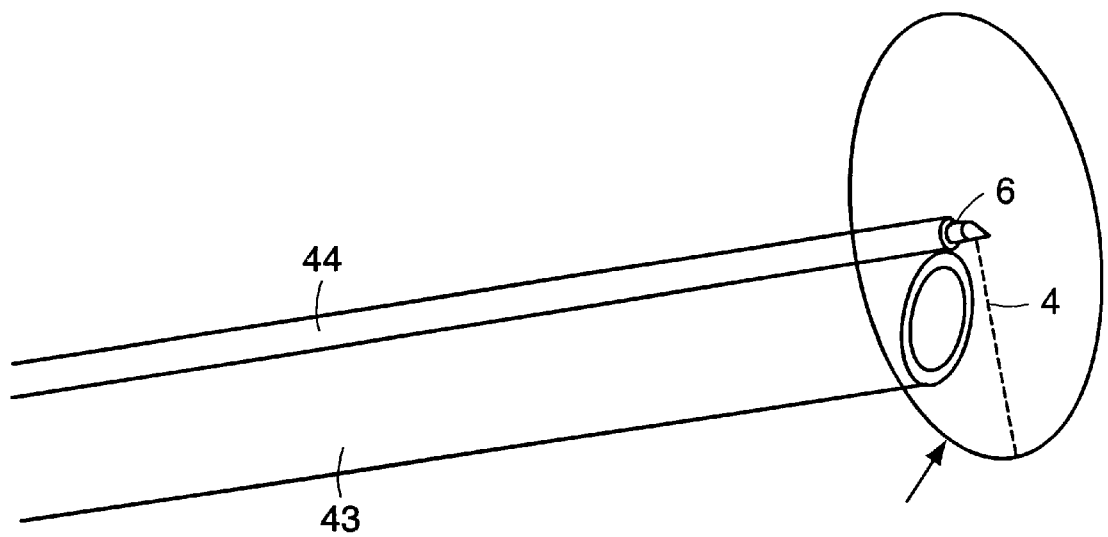

In a further embodiment of the invention shown in FIGS. 9A–B, the fiber optic needle probe is provided as a two-channel needle assembly and consists of a first and second housing, 43 and 44, defining a first and second channel, respectively. The first housing, or biopsy channel 43, functions as a hollow needle for aspirating tissue, while the second housing, or optical fiber channel 44, houses the optical fiber 11 and the distal optical element(s) which comprise the beam director 6. The optical fiber 11 is either inserted into the optical fiber channel 44 or is integrated directly into the second housing 44. The beam director 6 of the fiber optic needle probe may extend beyond the distal tip of the two-channel needle assembly such that it can perform cross-sectional imaging at, or near, the end of the portion of the two-channel needle assembly used for aspirating tissue.

Integration with a Core Biopsy Device

FIGS. 10A and 10B show an embodiment of the invention in which the fiber optic needle probe comprises a coring biopsy device. In this embodiment, the fiber optic needle probe is in the form of a two-channel needle assembly comprising a first housing configured as a core biopsy device 49. The channel of the second housing, optical fiber housing 51, can either extend the length of the first housing or can terminate near the section of first housing near a slot 47 which is used for obtaining the core tissue or biopsy specimen. The core biopsy device 49 typically consists of a hollow outer casing 45 with an internal hollow tubular movable cutter 46 having a sharpened edge. The hollow outer casing 45 typically has one or more slots 47 cut into it which permit the tissue specimen to be drawn or sucked into the hollow portion 48 of the outer casing. After the tissue specimen is drawn into the interior of the hollow outer casing 45, the inner movable hollow tubular cutter 46 is advanced to cut a specimen or core of tissue. This core specimen is retained in the central part of the inner movable tubular cutter 46.

This design and related core biopsy designs have the advantage that they can be used to cut multiple tissue specimens or cores. As the entire core needle is placed in the tissue that is desired to be biopsied, the inner movable tubular cutter 46 is retracted and advanced to cut a core specimen of tissue. The process may be repeated with each subsequent core specimen being held in the hollow inner movable tubular cutter 46. When it is necessary to obtain the tissue core specimens, the hollow inner movable tubular cutter 46 is withdrawn and the tissue core specimens are extracted from the hollow inner cutter 46 by pushing them out with a solid wire or stylette. Alternately, the entire core needle biopsy device is withdrawn.

The optical fiber 11 is inserted into the second channel of the optical fiber housing 50. In one embodiment of the invention, the beam director 6 of the optical fiber 11 extends beyond the end of the optical fiber housing 50 to permit the optical beam 4 to be directed and scanned into the tissue and to collect backreflected or backscattered optical signals from the tissue as shown in FIG. 10A.

Alternately, in another embodiment of the invention, an opening 52 is provided in the optical fiber housing 50 which permits the optical beam 4 to be directed and scanned into the tissue as shown in FIG. 10B. The fiber optic needle probe performs cross-sectional imaging or takes other optical measurements of the internal microstructure of the tissue into which the two-channel needle assembly is inserted. These images or other optical measurement information can serve to guide the placement of the two-channel needle assembly to avoid injury to sensitive structures and allow the physician to determine the areas of tissue which should be biopsied.

Figure 11A:
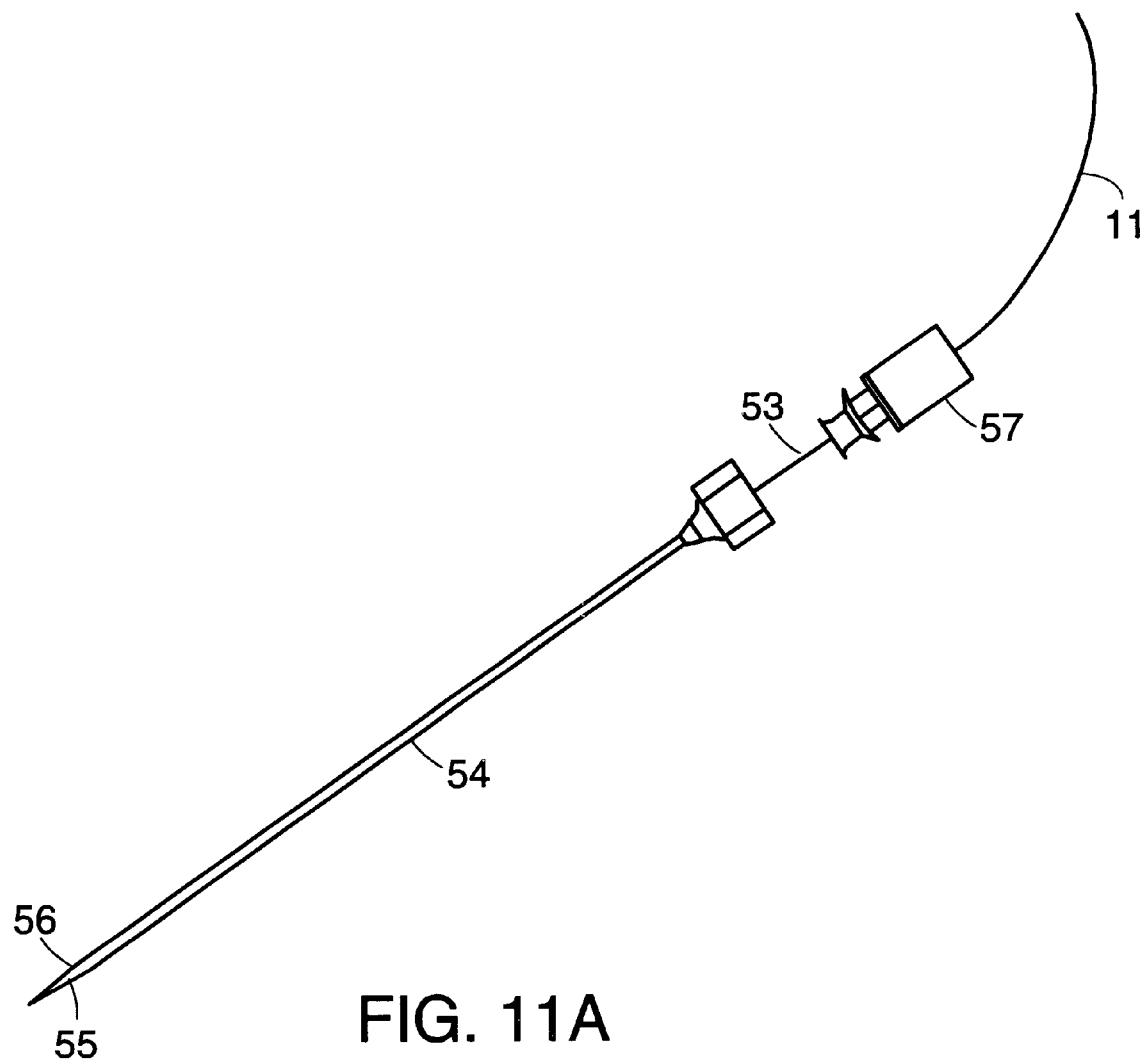
FIGS. 11A–C show an embodiment of the invention where the needle of the fiber optic needle probe comprises a coring tube within its bore and the optical fiber and beam director are positioned within the coring tube.
Figure 11B:
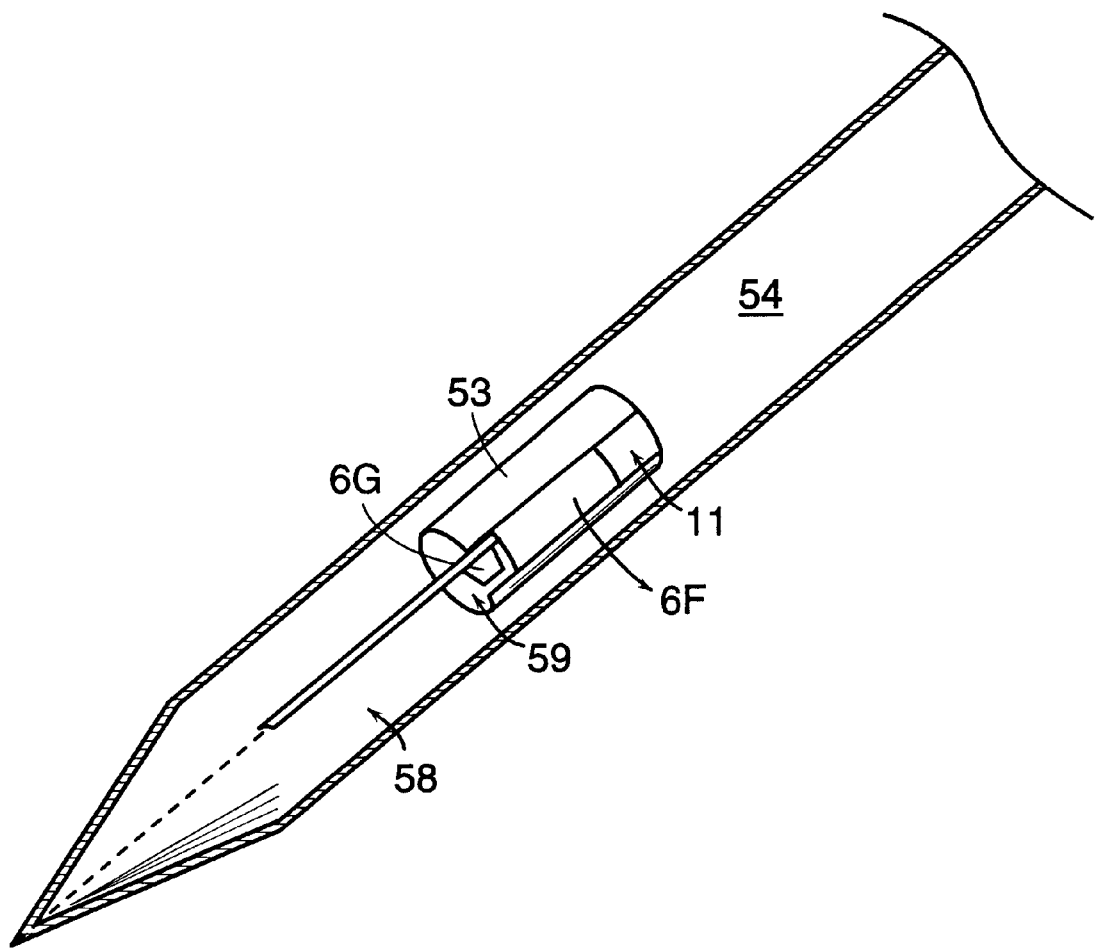
Figure 11C:
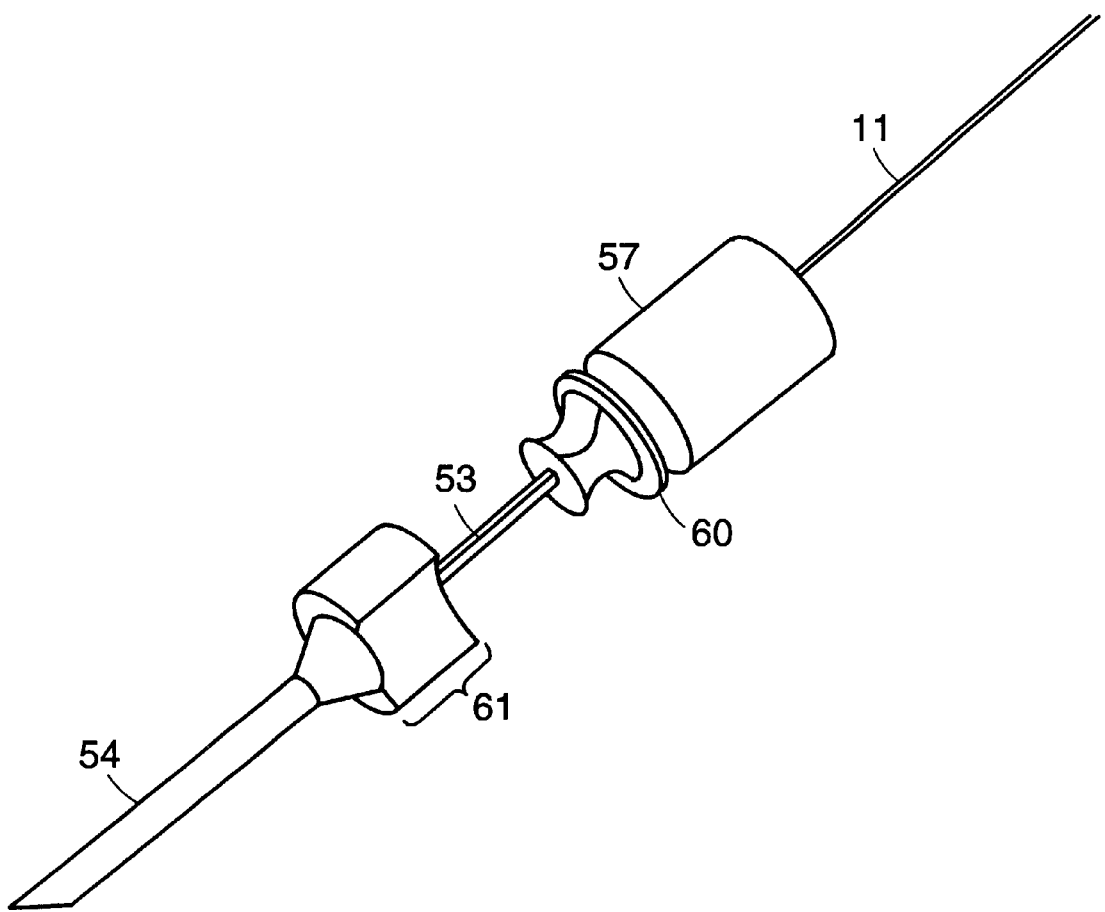

FIGS. 11A–C show an embodiment of the invention in which the fiber optical needle probe comprises a core biopsy needle 54 comprising a coring tube 53 and a needle assembly 55 comprising a cone-shaped tip 55t. A biopsy opening 56 is provided at the cone-shaped 55t and an actuator, in this example, a motor 57, is provided in proximity to the coring tube 53. FIG. 11B shows an enlarged view of a cut-away of the cone-shaped tip 55t. As can be seen from this view, the coring tube 53 extends substantially through the lumen 58 of the core biopsy needle 54 housing. The optical fiber 11 is positioned substantially within, or adjacent, the lumen 59 of the coring tube 53. Two optical elements comprise the beam director 6 in this embodiment. The optical fiber 11 itself comprises an integral lens 6F which is in optical communication with a 45 degree turning mirror 6G.

FIG. 11C shows an enlarged view of the coring tube 53 and motor 57. The coring tube 53 housing comprises a lure 60 which fits securely into the lure of an enlarged portion 61 of core biopsy needle housing 54. The flat parts of the lure 60 ensure proper registration of the coring tube 53 and needle assembly 55. Other arrangements, such as a bayonet or screw fitting, are also encompassed within the scope of the present invention. The coring tube 53 assembly and the needle assembly 55 can be integrated or part of separate devices.

Having thus described certain embodiments of the present invention, various alterations, modifications, and improvements will be obvious to those skilled in the art. Such variations, modifications and improvements are intended to be within the spirit and scope of the invention. The materials employed, as well as their shapes and dimensions, may be any required. Accordingly, the foregoing description is by way of example only and is not intended to be limiting. The invention is limited only as defined in the following claims and the equivalents thereto.

What is claimed is:

1. A fiber optic needle probe for use in optical coherence tomography imaging, the fiber optic needle probe comprising:

a needle having a wall defining a bore, said needle being sized and shaped for nonintraluminal insertion into a specimen;

a single substantially single-mode optical fiber, at least a portion of which is positioned within said bore; and a focusing element and beam director in optical communication with said optical fiber and being capable of directing light from said optical fiber to an internal structure within said specimen and collecting and directing light received from said internal structure to said optical fiber, wherein said single substantially single-mode optical fiber transmits light from a light source to said internal structure to illuminate said internal structure, wherein said single substantially single-mode optical fiber transmits said light received from said internal structure to an imaging apparatus utilizing optical coherence tomography.

2. The fiber optic needle probe of claim 1, wherein said beam director extends beyond the tip of said needle.

3. The fiber optic needle probe of claim 1, wherein said optical fiber is capable of moving independently within said bore.

4. The fiber optic needle probe of claim 1, wherein said optical fiber is fixedly positioned within said needle.

5. The fiber optic needle probe of claim 1, wherein said needle is an at least partially transparent cannula.

6. The fiber optic needle probe of claim 1, further comprising an actuator, wherein said actuator is in communication with at least one of said needle, said optical fiber, and said beam director, and wherein said actuator is capable of moving at least one of said needle, said optical fiber, and said beam director so as to scan said internal structure of said specimen.

7. The fiber optic needle probe of claim 6, wherein said actuator is capable of rotating at least one of said optical fiber, said beam director, and said needle.

8. The fiber optic needle probe of claim 6, wherein said actuator device is a motor coupled to said wall of said needle, said motor further comprising:

a magnet; and a coil, wherein at least one of said magnet or said coil is capable of movement, and wherein at least one of said magnet or said coil is coupled with said optical fiber and capable of causing a scanning motion of said optical fiber.

9. The fiber optic needle probe of claim 1, wherein said wall comprises an optical port.

10. The fiber optic needle probe of claim 9, wherein said beam director is positioned within said bore in close juxtaposition to said optical port.

11. The fiber optic needle probe of claim 9, wherein said optical port permits transmission of said light directed to said internal structure and reception of said light directed from said internal structure at a plurality of positions substantially collinear with a longitudinal axis of said needle.

12. The fiber optic needle probe of claim 9, wherein said optical port permits transmission of said light directed to said internal structure and reception of said light directed from said internal structure over a range of positions orthogonal to a longitudinal axis of said needle.

13. A two-channel needle assembly comprising:
- a first housing defining a first channel and comprising an extracting device;
- a second housing defining a second channel, said second housing in close juxtaposition to said first housing, said first and second housing being sized and shaped for nonintraluminal insertion into a specimen;
- a single substantially single-mode optical fiber positioned substantially within said second channel of the second housing; and
- a beam director and focusing element in optical communication with said single substantially single-mode optical fiber and being capable of directing light from said single substantially single-mode optical fiber to a segment of said specimen and directing light received from said segment to said optical fiber,
- wherein said specimen is in proximity to said extracting device,
- wherein said single substantially single-mode optical fiber transmits light from a light source to illuminate said segment of said specimen, and
- wherein said single substantially single-mode optical fiber transmits said light received from said segment of said specimen to an optical coherence tomography imaging device.

14. The two-channel needle assembly of claim 13, wherein said specimen is a tissue and said extracting device is capable of aspirating said tissue.

15. The two-channel needle assembly of claim 13, wherein said specimen is a tissue, and said extracting device comprises a movable cutter positioned within said first channel capable of cutting a core of said tissue.

16. The two-channel needle assembly of claim 13, further comprising an actuator;
- wherein said actuator is in communication with at least one of said first housing, said second housing, said optical fiber and said beam director, and
- wherein said actuator is capable of moving at least one of said second housing, said optical fiber, and said beam director so as to scan said internal structure of said specimen.

17. The two-channel needle assembly of claim 13, wherein said second housing is coaxial with said first housing.

18. An optical imaging system for use in optical coherence tomography, the optical imaging system comprising:
- a needle having a wall defining a bore, said needle being sized and shaped for nonintraluminal insertion into a specimen;
- a single substantially single-mode optical fiber substantially positioned within said bore;
- a focusing element and beam director in optical communication with said optical fiber and being capable of directing light from said optical fiber to an internal structure within said specimen and collecting and directing light received from said internal structure to said optical fiber; and
- an actuating device in communication with at least one of said needle, said optical fiber, and said beam director, said actuating device being capable of moving at least one of said needle, said optical fiber and said beam director, so as to scan said internal structure of said specimen and produce a measurement thereof,
- wherein said single substantially single-mode optical fiber transmits light from a light source to said internal structure to illuminate said internal structure,
- wherein said single substantially single-mode optical fiber transmits said light received from said internal structure to an imaging apparatus utilizing optical coherence tomography.

19. A method for guiding a biopsy instrument using a fiber optic needle probe, said method comprising the steps of:
- nonintraluminally introducing a fiber optic needle probe into a tissue, said needle probe including a single, single-mode optical fiber adapted to direct light to and from said tissue;
- measuring optical properties of a portion of said tissue based on the light directed by said optical fiber from said tissue; and
- guiding a biopsy instrument into said portion of said tissue based on said optical properties measured.

20. The method of claim 19, further comprising the step of extracting a sample from said tissue.

21. The method of claim 19, wherein said biopsy instrument is a hollow needle aspirator.

22. The method of claim 19, wherein said biopsy instrument is a coring device.

* * * * *